United States Patent
Gevins et al.

(12) 
(10) Patent No.: US 6,434,419 B1
(45) Date of Patent: Aug. 13, 2002

(54) NEUROCOGNITIVE ABILITY EEG MEASUREMENT METHOD AND SYSTEM

(75) Inventors: Alan S. Gevins; Michael E. Smith, both of San Francisco, CA (US)

(73) Assignee: SAM Technology, Inc., San Francisco, CA (US)

( * ) Notice: Subject to any disclaimer, the term of this patent is extended or adjusted under 35 U.S.C. 154(b) by 18 days.

(21) Appl. No.: 09/603,218

(22) Filed: Jun. 26, 2000

(51) Int. Cl.[7] .................................................. A61B 5/00
(52) U.S. Cl. ....................................................... 600/544
(58) Field of Search ................................. 600/544, 545, 600/587

(56) References Cited

U.S. PATENT DOCUMENTS

| | | | |
|---|---|---|---|
| 3,809,069 A | | 5/1974 | Bennett |
| 4,203,452 A | | 5/1980 | Cohen |
| 4,736,751 A | | 4/1988 | Gevins et al. |
| 5,038,782 A | | 8/1991 | Gevins et al. |
| 5,295,491 A | * | 3/1994 | Gevins ........................ 128/731 |
| 5,339,826 A | | 8/1994 | Schmidt et al. |
| 5,447,166 A | * | 9/1995 | Gevins ........................ 128/731 |
| 5,513,649 A | | 5/1996 | Gevins et al. |
| 5,724,987 A | * | 3/1998 | Gevins et al. ............... 128/731 |

* cited by examiner

*Primary Examiner*—Max Hindenburg
(74) *Attorney, Agent, or Firm*—Fay Kaplun & Marcin LLP; Eliot S. Gerber

(57) ABSTRACT

An efficient, objective testing method and system for evaluating mental acuity and changes in mental acuity is described. The method and system are based on measuring an individual's behavioral responses and brain function during a brief test of working memory and passive control condition. The method and system is designed to assess an individual's overall cognitive ability ("general intelligence"), and whether that overall cognitive ability has been significantly affected by a variety of factors such as progressive disease processes, medication, stress, fatigue or training. The method and system can be used to determine whether drugs being evaluated to treat diseases or conditions affecting higher cognitive brain function have a significant positive effect on delaying or improving the symptoms of such a disease or condition, especially during clinical trials for drug approval and subsequent marketing. The method and system may also be employed as part of the successful diagnosis or ongoing treatment of neurological diseases or conditions that directly or indirectly affect human neurocognitive performance. The method and system may also be used to determine transitory changes in overall cognitive ability due to emotional stress or fatigue, and more long lasting changes in overall cognitive ability following training and educational programs.

26 Claims, 13 Drawing Sheets

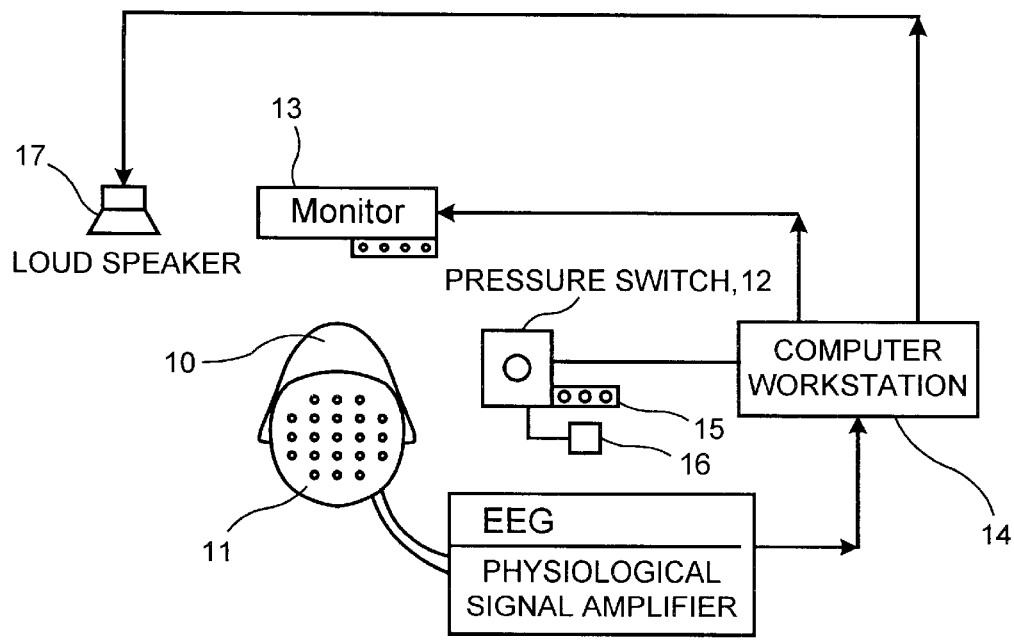
F I G. 1
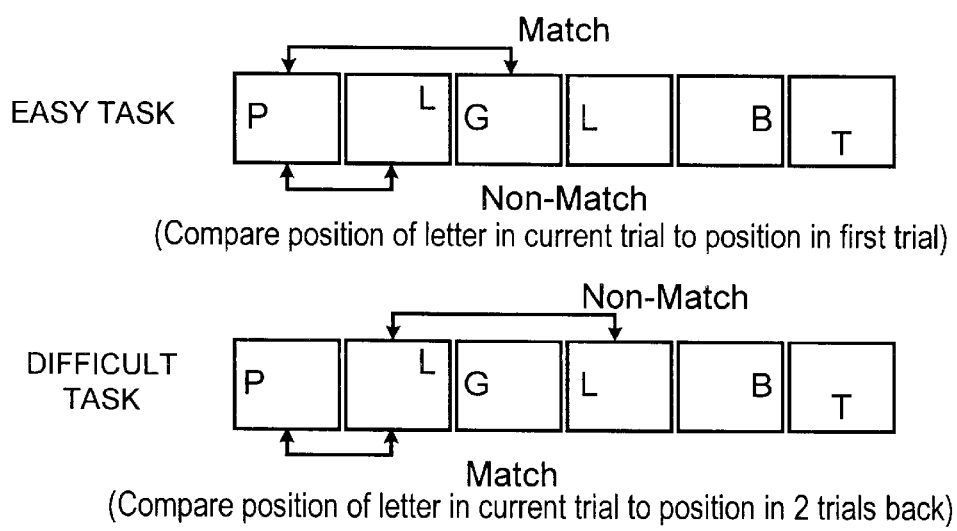
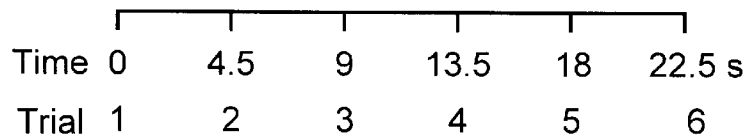
F I G.2

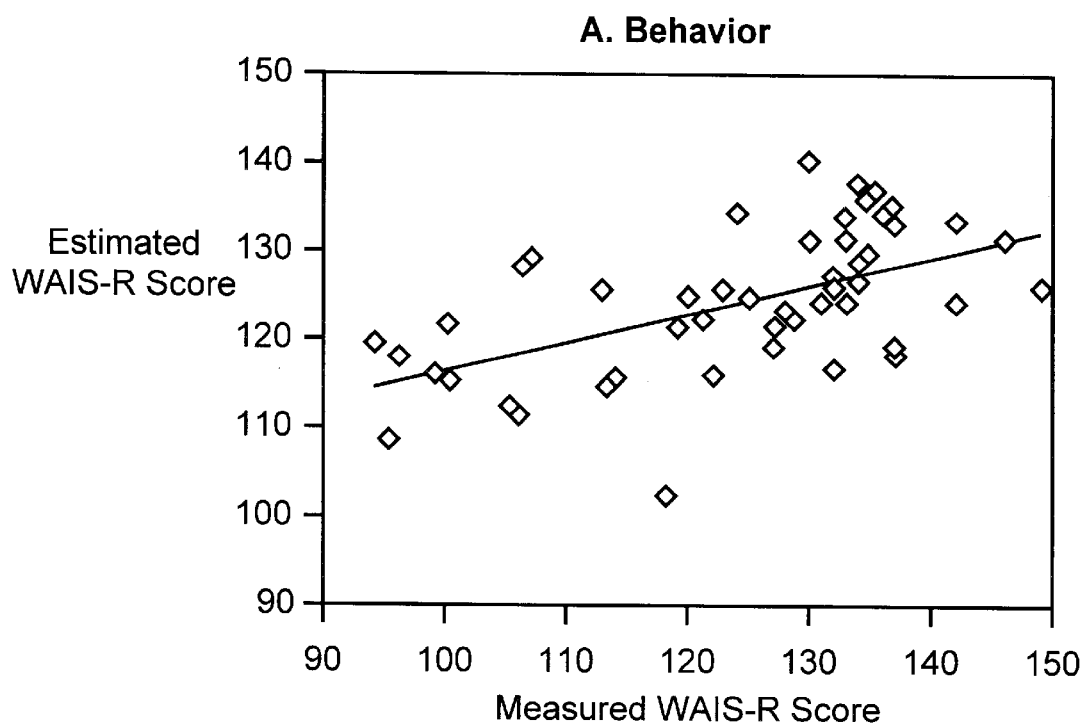
F I G. 7A
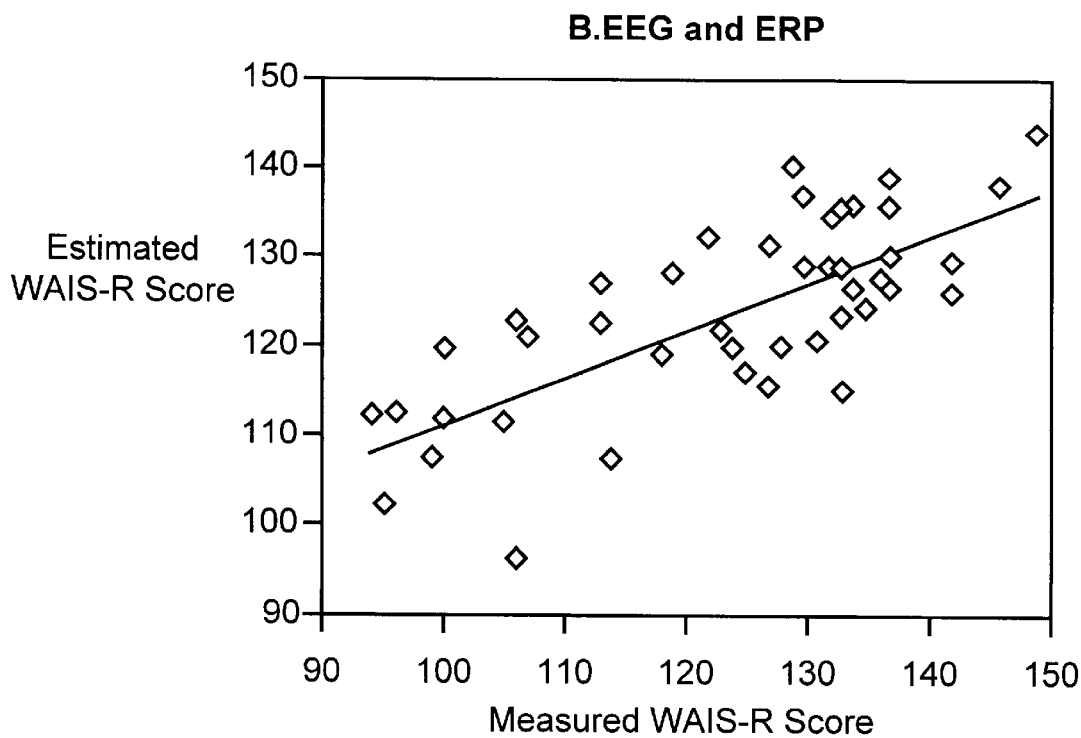
F I G. 7B ically due to
NEUROCOGNITIVE ABILITY EEG MEASUREMENT METHOD AND SYSTEM This invention was made with government support under contract F49620-94-C-0017 awarded by the Air Force Office of Scientific Research. The government has certain rights in the invention.

BACKGROUND OF THE INVENTION

1. Field of the Invention

The present invention relates to psychometric, neuropsychological and neurophysiological tests for measuring mental acuity and more particularly to the use of electroencephalogram (EEG) recordings for such measurements.

2. Description of the Related Art

There is currently no method that quickly and objectively measures an individual's overall cognitive ability. Nor is there a method that is able to do so on repeated occasions in order to measure changes in overall cognitive ability due to disease, injury, or other conditions affecting higher cognitive brain functions, or such changes due to remedial treatment. A person's overall cognitive ability, often called "general intelligence," is considered an attempt to quantify analytic cognitive ability. It does not measure other types of intelligence i.e., creative and practical, or "multiple intelligences" i.e., linguistic, musical, bodily/kinesthetic, emotional, interpersonal and intrapersonal.

The presently available various psychometric tests of overall cognitive ability, such as the Weschler Adult Intelligence Scale (WAIS) or Raven's Progressive Matrices, each suffer from one or more deficiencies. These deficiencies include cultural bias, subjective interpretation, excessive test length, high cost, and lack of assessment of the subject's motivational factors in performing the test. Also, most test instruments lack multiple applications of the test that would be needed for repeated testing. Additionally, no psychometric test provides direct information about the subject's actual brain function and hence supplies no information relative to the putative pharmacological action of a drug, disease, injury or therapy which is being studied. This lack of suitable tests is a major barrier to long term assessment of changes in an individual's level of overall cognitive ability. This assessment is of paramount importance in evaluating the success of a putative treatment for any form of treatment affecting higher cognitive brain functions, for example drugs to aid memory in elderly patients. In principle direct measurement of brain functions underlying overall cognitive ability, by EEG measurements of brain wave activity, could overcome these deficiencies. Prior attempts at such EEG measurements, however, have not been fruitful because of two major shortcomings. First, there was the failure to measure brain activity while the subject performed a task taxing the subject's mental processes, such as working memory, that are highly related to overall cognitive ability. Merely recording brain activity while the subject sits idly, watching a meaningless flashing light, or performing a task not requiring her or his full attention is insufficient to produce patterns of brain activity characterizing individual differences in overall cognitive ability or changes in an individual's overall cognitive ability over an extended time period. Second, there was a reliance on single, overly simplistic measures of brain function derived from theoretical constructs without sufficient support from empirical data. For instance, although it may seem reasonable a priori that higher overall cognitive ability should be associated with faster brain processing, it is not necessarily true that a measure of the speed of brain processing is actually sufficient to characterize individual differences in overall cognitive ability.

In Schmidt et al., U.S. Pat. No. 5,339,826, the effectiveness of video-taped training material is tested using EEG. In one method, the student's brain wave alpha and beta band activity is analyzed to determine attention and cognitive activity. In another method EP (Evoked Potential) responses are measured using multiple choice questions.

In Cohen U.S. Pat. No. 4,203,452 a single channel of EEG is measured in an attempt to ascertain if a student is undergoing short-term learning or long-term learning.

In Gevins U.S. Pat. No. 5,447,166 EEG signals are used to alter a computer program, i.e. present more or less difficult test material to the user.

Bennett U.S. Pat. No. 3,809,069 seeks to measure the intelligence of a subject using pulsed stimuli to evoke the subject's responses, which are compared to the frequencies of responses of others.

These patents, and the other references cited, are incorporated by reference herein.

SUMMARY OF THE INVENTION

In accordance with the present invention, a novel method and system called "Neurocognitive Ability Measurement System" is provided for testing the brain activity of subjects while they perform a simple cognitive task in order to measure overall cognitive ability.

The main advantage of this system is that, by measuring neurological signals of basic cognitive processes underlying overall cognitive ability, it is able to determine a subject's cognitive ability quickly, objectively, without cultural bias, and on repeated occasions. This differs from current psychometric intelligence tests that are lengthy, subjectively interpreted, depend in part upon culturally specific knowledge and are not designed to be used for repeated testing of the same person. The "Neurocognitive Ability Measurement System" also differs from prior attempts to use measures of brain activity to characterize cognitive ability in a number of essential respects. First, prior methods did not record brain activity while a subject performed a task engaging specific cognitive functions, such as working memory, that are highly related to overall cognitive ability. Thus, the prior measures were not specific to higher intellectual functioning. Second, prior methods only used single measurements of brain function to predict cognitive ability, and consequently had only a modest correlation with a subject's overall cognitive ability. By contrast, the "Neurocognitive Ability Measurement System" combines several independent measurements of brain function and consequently produces a high correlation with a subject's overall cognitive ability as measured with a standard psychometric test. Third, in estimating overall cognitive ability, prior methods that measured brain activity did not consider the speed or accuracy of a subject's performance of a cognitive task, further restricting the test's accuracy. The "Neurocognitive Ability Measurement System" combines measures of both brain function and task performance to achieve a more accurate prediction of a subject's cognitive ability.

The system operates as follows: the subject is tested while performing a simple cognitive task as his or her brain waves are recorded. The subject's overall cognitive ability ("general intelligence") is computed by combining task performance measures and brain wave measures according to a formula previously determined from a normative group of subjects of the same age range.

The system uses a digital computer workstation having a screen and a response input device, and an EEG device (electroencephalograph) to measure the brain waves of the subject. The EEG device also measures eye and scalp muscle activity and head movements in order to determine whether and how the brain waves are contaminated by artifacts. The system either removes such contaminants when possible or else discards the contaminated data. The subject is presented with a brief task on the screen that tests a fundamental cognitive function that is highly related to overall cognitive ability, preferably the function of working memory. (Working memory refers to the limited capacity to control attention and sustain its focus on a particular active mental representation for several seconds. This ability plays an important role in comprehension, reasoning, planning, and learning.) A subject's behavioral responses and brain waves are measured as she or he performs a series of repetitions of easy and more difficult versions of the task. The subject's brain waves are also recorded at rest for comparison with data recorded during performance of the task. A plurality of primary measures are computed from the data, preferably including: 1) the subject's reaction time to each task trial; 2) the accuracy of the subject's response to each task trial; 3) the amplitude of the subject's EEG alpha band activity recorded over parietal and prefrontal cerebral cortical brain regions; 4) the amplitude of the subject's EEG frontal midline theta activity; 5) the peak time of the subject's fronto-central P200 and P300 averaged evoked potential peaks elicited by the task stimuli; 6) the peak amplitude of the subject's fronto-central P200 and P300 averaged evoked potential peaks elicited by the task stimuli; 7) the amplitude of the subject's frontal delta power associated with slow horizontal eye movements; 8) the amplitude of the subject's posterior theta and delta powers; 9) ratios of the subject's posterior theta to alpha power; 10) ratios of each of primary measures 1–6 and 9 between different locations on the scalp; and 11) measures of covariance, correlation or coherence of primary measures 3 and 4, and of the P200 and P300 amplitudes, between different locations on the scalp. Secondary measures are then computed preferably including: 1) differences in the primary measures between resting and the easy task version; 2) differences in the primary measures between easy and more difficult task versions; 3) differences in the primary measures between initial and subsequent repetitions of the task in the same session; and 4) differences in secondary measures 1 and 2 between initial and subsequent repetitions of the task in the same session. The preceding procedure of collecting and analyzing data is repeated over a normative group of subjects. Equations are then computed, preferably using a multiple regression or neural network algorithm. The equations consist of weighted combinations of some or all of the primary and secondary measures that best predict the overall Weschler Adult Intelligence Scale (WAIS) score of each member of the group. The output of these equations are called Neurocognitive IQ (NIQ) scores. The NIQs of a new subject are then determined by first measuring her or his behavioral responses and EEG while performing the same cognitive tasks, then computing the appropriate primary and secondary measures, and finally weighting them according to the equation determined from the normative group. If the subject has been previously tested with the "Neurocognitive Ability Measurement System," the system can compare her or his current NIQs with prior test results to determine whether there has been a change.

Objectives of the present invention are to provide a method and system to:

1. Measure overall cognitive ability ("general intelligence") quickly, objectively, inexpensively and with minimal cultural bias;
2. Repeatedly measure overall cognitive ability of a subject in order to measure changes due to diseases, injury, fatigue, or other conditions, or treatment with drugs or other remedial therapies;
3. Repeatedly measure overall cognitive ability in order to measure changes due to training, learning, or use of drugs that improve brain function or slow the progression of diseases or conditions which affect higher cognitive brain functions.

It is a feature of the present invention to measure neurophysiological signals underlying overall cognitive ability while subjects are at rest and while they perform tasks engaging basic cognitive processes, such as working memory, that are predictive of overall cognitive ability.

It is a further feature of the present invention that the tasks used for testing do not depend on prior knowledge that is likely to be culturally biased, such as reading a particular language or making use of information derived from a particular cultural context.

It is a further feature of the present invention to use an easy and a more difficult version of a task for testing in order to apply a calibrated difference in mental workload to the subject from which the subject's mental effort and amount of brain utilization can be estimated.

It is a further feature of the present invention to measure behavioral performance, such as performance accuracy and speed, while performing the cognitive tasks.

It is a further feature of the present invention to measure neurophysiological signals characterizing the subject's mental effort and amount of brain utilization to perform the cognitive tasks.

It is a further feature of the present invention to measure neurophysiological signals characterizing the subject's sustained focused attention while performing the cognitive tasks.

It is a further feature of the present invention to measure neurophysiological signals characterizing the subject's neurocognitive strategy while performing the cognitive tasks.

It is a further feature of the present invention to measure neurophysiological signals characterizing the subject's cognitive speed and transient focused attention while performing the cognitive tasks.

It is a further feature of the present invention to measure neurophysiological signals characterizing the subject's alertness while performing the cognitive tasks and during the resting control tasks.

It is a further feature of the present invention to measure behavioral performance differences between performing an easy and a more difficult version of the cognitive task, and to measure differences in neurophysiological signals between resting, easy and difficult task versions, in order to measure how the subject's brain and behavior respond to changes in mental workload imposed by the tasks.

It is a further feature of the present invention to measure changes in neurophysiological signals as a subject performs repeated trials of the cognitive tasks during one test session in order to characterize how quickly the subject's brain adapts to the challenge imposed by the tasks.

It is a further feature of the present invention to measure differences in neurophysiological signals and cognitive task performance between initial and subsequent trials of an easy and a more difficult version of a cognitive task during one test session in order to measure how quickly the subject's brain and behavior adapt to changes in mental workload imposed by the task.

It is a further feature of the present invention to compare measurements of neurophysiological signals and cognitive task performance between successive test sessions to determine whether the subject's neurophysiological signals and cognitive task performance have changed due to an underlying clinical condition thus allowing detection of the aforementioned condition.

It is a further feature of the present invention to compare measurements of neurophysiological signals and cognitive task performance between successive test sessions to determine whether the subject's neurophysiological signals and cognitive task performance have changed and continue to change when under the influence of an administered drug.

It is a further feature of the present invention to compare measurements of neurophysiological signals and cognitive task performance between successive test sessions to determine whether the subject's neurophysiological signals and cognitive task performance have changed and continue to change under a regime of any non-drug related therapy meant to enhance such performance.

It is a further feature of the present invention to measure a multivariate combination of neurophysiological signals and cognitive task performance that, taken together, are empirically predictive of overall cognitive ability under well-controlled testing conditions.

It is a further feature of the present invention to determine overall cognitive ability score or scores by combining measurements of speed and accuracy of task performance with brain wave (electroencephalogram or EEG) measurements of alertness, focused attention, brain utilization, neurocognitive strategy, cognitive speed and transient focused attention, combinations of differences in the preceding measurements between resting and easy and more difficult cognitive task versions, and combinations of differences in the preceding measurements between initial and subsequent trials of the cognitive task during one test session.

It is a further feature of the present invention that the overall cognitive ability scores predicted by the multivariate combination of neurophysiological signals and cognitive task performance is the overall intelligence quotient as measured on a standard cognitive ability test such as the Weschler's Adult Intelligence Scale.

It is a further feature of the present invention to test the overall cognitive ability of a subject by combining the above mentioned measurements according to equations previously determined on a normative group of subjects performing the same cognitive tasks and having the same neurophysiological and cognitive performance variables measured.

It is a further feature of the present invention to provide a method and system to determine the overall cognitive ability of a subject by measuring the subject's brain waves while the subject performs a task that, for instance, engages the basic cognitive function of working memory.

It is a further feature of the present invention that the method and system supplies neurophysiological measurements that allow determination of the pharmacological effect of an administered drug on the aforementioned parameters of neurophysiological and cognitive performance, and thus aspects of any drug's pharmacological action on the brain, including the ongoing assessment of such pharmacological action on the brain.

BRIEF DESCRIPTION OF THE DRAWINGS

Other objectives and features of the present invention will be apparent from the following detailed description, taken in conjunction with the accompanying drawings. In the drawings:

FIG. 1 is a schematic diagram of the system used in the present invention;

FIG. 2 is a diagram of the working memory task;

FIG. 7A is a graph showing stepwise multiple regression using eight working memory and sustained focused attention task performance variables to produce an estimate of test scores (vertical axis) that is significantly correlated (R=0.56) with scores on the Weschler Adult Intelligence Scale-Revised (horizontal axis). This graph illustrates Experiment 1.

FIG. 7B is a graph showing stepwise multiple regression using eight neurophysiological (EEG and ERP) variables to produce an estimate of test scores (vertical axis) that is more highly correlated (R=0.73) with scores on the Weschler Adult Intelligence Scale-Revised (horizontal axis) than that produced by the behavioral variables shown in FIG. 7A. This graph illustrates Experiment 1.

DETAILED DESCRIPTION OF THE INVENTION

Figure 3A:
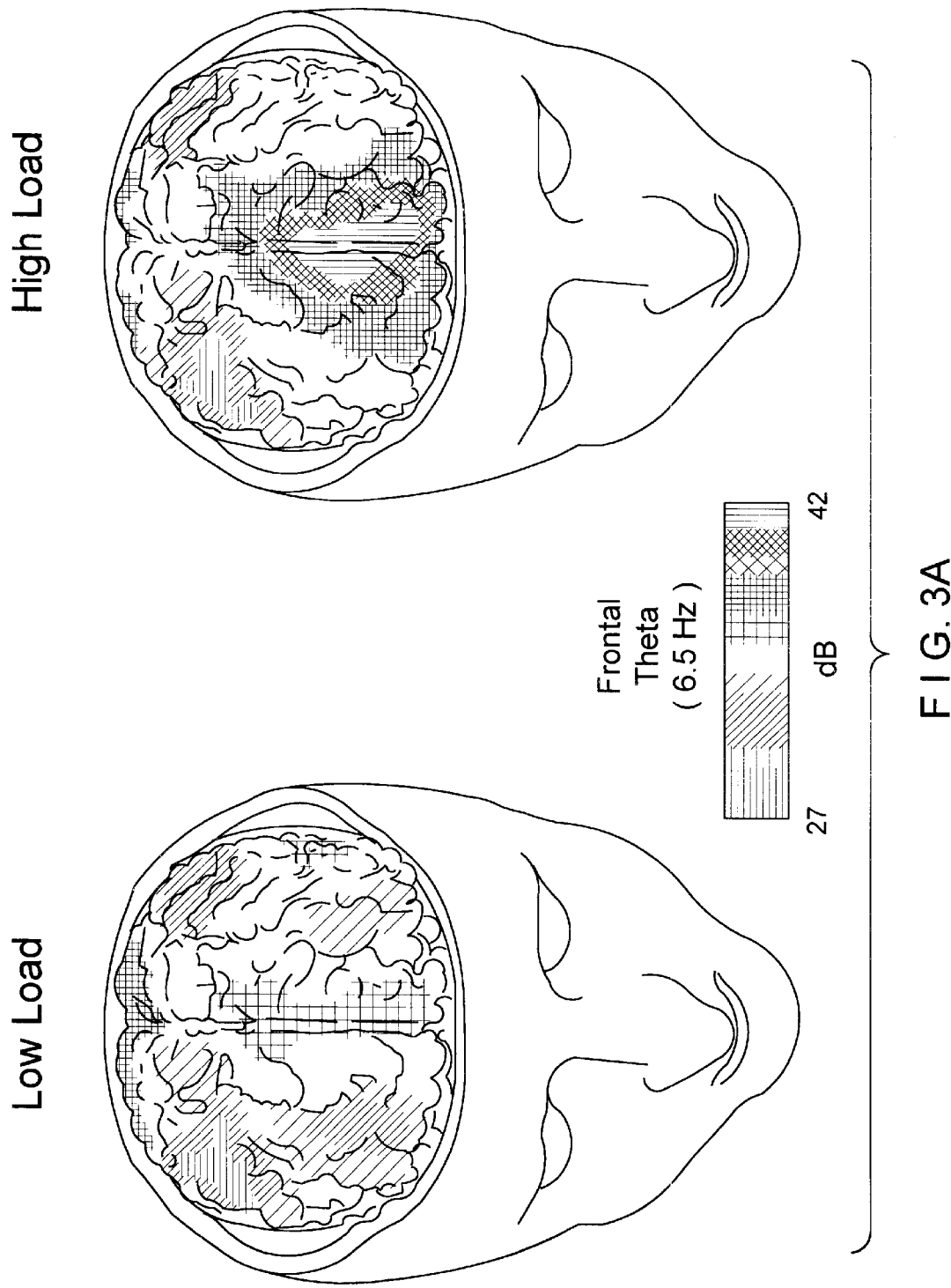
FIG. 3A shows two images of the top of a head with the brain exposed. They illustrate the effect of varying the load (difficulty) of a working memory task on the magnitude of the frontal midline theta band EEG signal, a signal of sustained focused attention.

The present invention is illustrated in FIG. 1. As shown therein, a human subject 10, whose head is illustrated, wears a cloth hat 11, or headset having electrode leads which contact the scalp of the subject. The leads detect the subject's weak analog brain waves and also the electrical activity of his eyes and scalp muscles. A suitable EEG hat is described in the inventor's U.S. Pat. No. 5,038,782, issued Aug. 13, 1991. The hat has preferably 1–32 independent electrodes, although more electrodes may be used. The brain waves are amplified, preferably as described in the U.S. Pat. No. 5,038,782 and artifacts detected and removed, for example, as described in the inventor's U.S. Pat. No. 4,736,751 issued Apr. 12, 1988 and entitled "Brain Wave Source Network Location Scanning Method and System," and as described in the inventor's U.S. Pat. No. 5,513,649 issued May 7, 1996 and entitled "Adaptive Interference Canceler for EEG Movement and Eye Artifacts," all of which are incorporated by reference herein.

Simultaneously with the detection of the subject's brain waves and other physiological signals, the subject is presented with tasks that test fundamental cognitive functions that are highly related to overall cognitive ability, preferably the function of working memory, for example as described in Gevins et al, 1998, 1997, 1996, in McEvoy, Smith and Gevins, 2000, 1998, and in Smith, McEvoy, and Gevins, 1999. A series of trials of preferably easy and more difficult versions of the task is presented. The task is presented preferably on the screen 13 of a computer monitor, or by a loudspeaker 17 connected to the digital computer workstation 14. The subject regards the monitor screen or listens to the loudspeaker and responds using a keyboard key 15, or alternatively a switch 12 or a joystick 16. An example of a working memory task is set forth in detail below. For comparison, the subject's brain waves are also recorded briefly while he or she rests with eyes open and eyes closed.

Following completion of the task, the task performance and EEG data are analyzed to extract summary measures from the data as described in Gevins, et al., 1998, 1997, 1996, and Gevins and Smith, 1999.

A plurality of primary measures are computed from the data, preferably including: 1) the subject's reaction time to each task trial; 2) the accuracy of the subject's response to each task trial; 3) the amplitude of the subject's EEG alpha band activity recorded over parietal and prefrontal cerebral cortical brain regions, 4) the amplitude of the subject's EEG frontal midline theta activity; 5) the peak time of the subject's fronto-central P200 and P300 averaged evoked potential peaks elicited by the task stimuli; 6) the peak amplitude of the subject's fronto-central P200 and P300 averaged evoked potential peaks elicited by the task stimuli; 7) the amplitude of the subject's frontal delta power associated with slow horizontal eye movements; 8) the amplitude of the subject's posterior theta and delta powers; 9) ratios of the subject's posterior theta to alpha power; 10) ratios of each of primary measures 1–6 and 9 between different locations on the scalp; and 11) measures of covariance, correlation or coherence of primary measures 3 and 4, and of the P200 and P300 amplitudes, between different locations on the scalp. Secondary measures are then computed preferably including: 1) differences in the primary measures between resting and the easy task version; 2) differences in the primary measures between easy and more difficult task versions; 3) differences in the primary measures between initial and subsequent repetitions of the task in the same session; and 4) differences in secondary measures 1 and 2 between initial and subsequent repetitions of the task in the same session.

Weighted combinations of some or all of the primary and secondary measures are then computed, resulting in Neurocognitive IQ (NIQ) scores. If the subject has been previously tested with the "Neurocognitive Ability Measurement System," the system can compare her or his current NIQs with prior test results to determine whether there has been a significant change, for instance due to the side effects of a medication. The weightings for the equations used to compute a subject's NIQs are previously determined on a normative group of healthy subjects of the same age range as the subject being tested. Each member of this normative group had his/her cognitive ability measured with a standard psychometric test of cognitive ability, preferably the Weschler Adult Intelligence Scale (WAIS). They then performed the same cognitive tasks that test fundamental cognitive functions highly related to overall cognitive ability, preferably the function of working memory, while their brain waves were measured and the above mentioned primary and secondary measures were extracted. Equations were computed, preferably using a multiple regression or neural network algorithm, that best predicted the overall score of each member of the group on the standard psychometric test.

The following description is of an experiment that measured Neurocognitive IQ scores in a group of 80 subjects.

Method and Results of Experiment I

Summary: Neurobehavioral variables associated with working memory ability predicted cognitive ability test scores in data from an ethnically diverse and gender matched sample of 80 subjects who performed working memory tasks concurrent with electroencephalogram recordings. The results demonstrate a close relationship between the neural processes used to maintain representations in working memory and scores obtained on a standard psychometric test of cognitive ability. The neurobehavioral measures also distinguished individuals with relatively high verbal cognitive ability from those with a relatively high nonverbal cognitive ability, and characterized them in terms of relative utilization of left and right cerebral hemispheres. These findings suggest the feasibility of developing objective and efficient neurological tests of cognitive ability that would be relatively insensitive to cultural influences.

Introduction: Tests of cognitive ability and aptitude are often criticized for relying heavily on assessment of a particular set of culturally influenced knowledge and skills. By contrast, some approaches to characterizing mental ability stress the diverse ways in which intelligence can be manifested and others the importance of measuring the fundamental cognitive functions that are central to learning and critical thinking. Here we illustrate a close relationship between neurobehavioral indices of a fundamental cognitive function and scores on a widely used intelligence test. This represents a step towards the development of tests of cognitive ability that are based on performance related brain function rather than specific education and cultural experience.

Central among fundamental cognitive functions is the consciously controlled, sustained attention process that supports the ability to keep information active in mind, and to use that information in the context of goal-directed activity. This ability, referred to as "working memory", is essential to the higher order thought processes involved with comprehension, reasoning, planning, and problem solving. Measures of working memory ability tend to be positively correlated with performance on psychometric tests of cognitive ability and other indices of scholastic aptitude.

Working memory appears to involve a functional network linking distributed regions of cerebral cortex. Activation of this network can be detected in measurements of neuroelectric activity recorded at the scalp. More specifically, a task-imposed change in working memory load tends to produce characteristic changes in the amplitude of spectral components of the ongoing electroencephalogram, and in components of the averaged brain potentials evoked by a stimulus. Individual differences in such responses can be construed as neural indices of individual differences in working memory ability. We have previously found that neuroelectric measures can be used to predict task performance accuracy. Here we report that scores on a widely used intelligence test can be predicted by combinations of behavioral and neuroelectric indices measured during performance of simple attention-demanding tasks that require working memory.

Figure 3B:
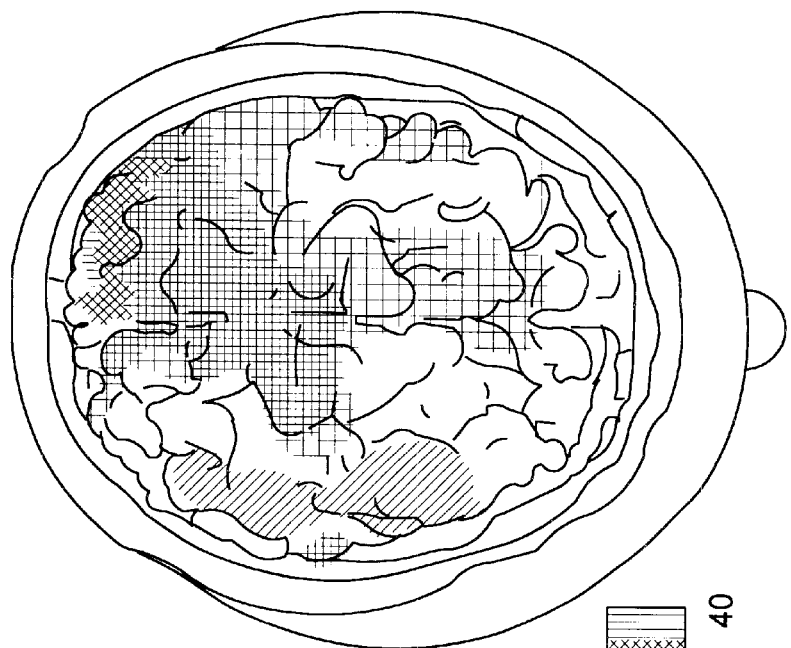
FIG. 3B shows two images of the top of the head with the brain exposed. They illustrate the effect of varying the load (difficulty) of a working memory task on the magnitude of the alpha band EEG signal, a signal inversely related to the amount of brain utilization.
Figure 3B:
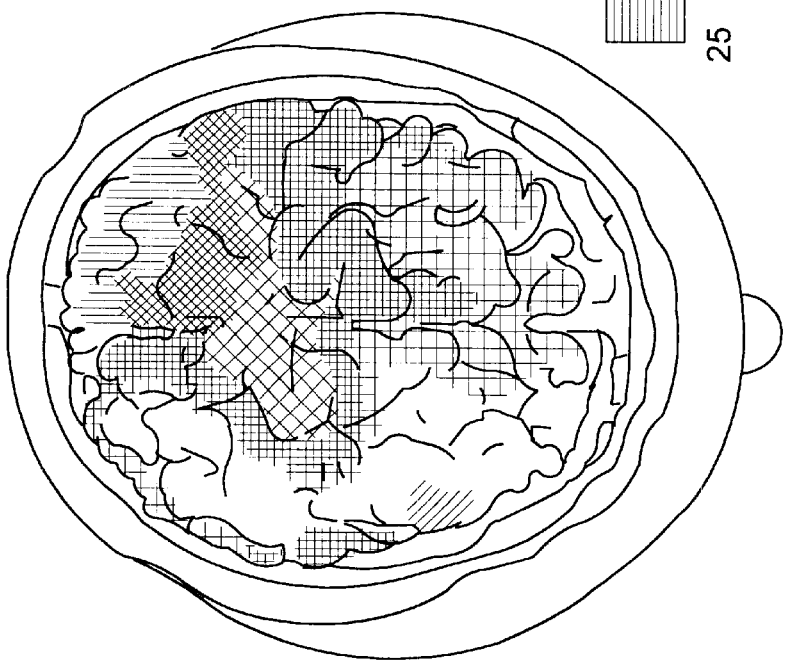

This investigation was in part motivated by recent findings that the human EEG is highly sensitive to the working memory demands of a task. Increases in working memory demands have been shown to modulate EEG spectral content. For example, signal power in the upper theta (5–7.5 Hz) frequency band over midline frontal cortex (FIG. 3A) increases in tasks with greater working memory requirements. This signal appears to be generated in the region of the anterior cingulate cortex, an important component of a frontal brain circuit involved with attention. Conversely, signal power in the lower alpha (8–10 Hz) frequency band over dorsolateral prefrontal and superior and inferior parietal cortex (FIG. 3B) decreases in tasks with greater working memory requirements. Alpha band signal strength is inversely related to the proportion of neurons in a population activated by task performance. That is, the alpha rhythm seems to represent a type of "cortical idling". The amplitude of some stimulus-elicited components of the average event-related potential (ERP) are sensitive to working memory task demands. For example, the P300 ERP component is elicited when task relevant stimuli are attended to and categorized and is increased in working memory tasks. It is thought to represent the transient focused attention required to integrate a stimulus with internal representations, and it appears to be generated in many cortical areas.

Methods and Procedures: To determine whether these neuroelectric signals of working memory are related to individual differences in cognitive ability, the EEG of 80 clinically normal and healthy, right-handed young adults was recorded during task performance. Participants had a mean age of 21.4 yrs (range 18–28 yrs), with 38 females and 42 males. All participants had completed high school, and they had a mean of 2.5 years of post-secondary education (range 0 to 7 years). Their ethnicity was statistically representative of the diversity of San Francisco Bay Area. These individuals performed variants of a task in which they viewed a series of letters presented one at a time at different locations on a computer screen (FIG. 2). The task required them to maintain and update representations of spatial information in working memory. In a difficult "high load" task variant, participants were required to indicate whether the screen position of the stimulus occurring on the current trial was the same as the position of the stimulus presented two trials previously. That is, participants were required to continuously monitor a stream of stimuli, maintain a representation of the last two stimulus positions in working memory, and update that representation each time a new stimulus was presented. Participants also performed an easier "low load" task that had equivalent stimulus and response requirements, but that only required matching each stimulus position to that of the first stimulus in each block of trials. Stimuli occurred at 4.5 sec intervals within each block of 23 trials. Eight blocks of trials were performed for each task, with brief rest breaks between blocks. During task performance, cortical activity was measured by recording the EEG at the scalp from 27 standard scalp electrodes with equivalent recording parameters and preprocessing for artifact removal according to the procedures described in Gevins et al, 1996, 1997, 1998, in McEvoy, Smith and Gevins, 2000, 1998, and in Smith, McEvoy and Gevins, 1999. Estimates of the power spectrum of the EEG were derived from 2-second windows and averaged over all data segments for each subject in each task condition. In addition, the EEG of each trial, aligned in time with the stimulus, was averaged over trials of each task variant to produce average ERPs. For statistical analyses, data from only a small subset of electrodes (those directly over lateral and midline dorsolateral prefrontal and parietal cortex) were used. Decisions concerning which electrodes to include in these analyses were based on results of the above-noted prior studies. Power of the frontal theta (6–7 Hz) signal was measured at an anterior midline (Fz) electrode. Power of the lower frequency (8–10 Hz) component of the alpha signal was measured at left (F3) and right (F4) frontal, and left (P3) and right (P4) superior parietal electrodes, and power of the higher frequency (10–12 Hz) alpha signal was measured at left (P7) and right (P8) inferior parietal electrodes. Amplitude and latency of the P300 ERP component were measured at a midline parietal electrode (Pz).

In order to measure overall cognitive ability ("general intelligence"), the Wechsler Adult Intelligence Scale Revised (WAIS-R) was administered to each participant. This test is the de facto standard clinical neuropsychological instrument used to assess cognitive ability. The WAIS-R is composed of eleven tests. These include six tests that are primarily verbal in nature, and five tests that are primarily nonverbal in nature. From the results of these tests three composite scores are derived. These include a total score intended to summarize cognitive ability, a "verbal" cognitive ability score, and a "performance" or "nonverbal" cognitive ability score. Each score is age-normalized with respect to a population mean of 100 (s.d.=15).

For entry into the study we required that participants have a WAIS-R total score of 85 or greater, and at least a high school diploma or equivalent. These requirements effectively eliminated potential participants with cognitive ability test scores below the average range. This was done for several reasons. First, we sought to avoid including individuals who might have clinically abnormal and hence easily distinguishable EEG patterns (undiagnosed brain damage or abnormality is one source of below average IQ test scores). Second, we sought to eliminate potential participants who might display excessively poor performance on the difficult working memory task, because it is difficult to readily distinguish performance deficits that are related to ability from those that arise from a lack of effort or compliance with task demands. Third, we sought to minimize any variance in the WAIS-R scores that might be more attributable to large educational differences than to ability differences. Together, these precautions allowed us to make a more rigorous evaluation of the hypothesis that EEG and performance variables would predict IQ test scores, and minimized the possibility that any observed results might only reflect abnormalities in the EEG or poor task performance.

In the experimental sample as a whole, total intelligence scores ranged from 94 to 149 (mean=121, s.d.=13.5), verbal scores ranged from 93 to 150 (mean=119, s.d.=13.8) and performance scores ranged from 93 to 140 (mean=117, s.d.=13.0). The verbal and nonverbal scores on the WAIS-R tend to be highly correlated. However, a variety of factors can contribute to differences between these scores, including cultural and educational differences. For example, the WAIS-R sub-tests that are most highly correlated with the verbal score, the vocabulary and information sub-tests, assess what has been referred to as "crystallized intelligence", that is, the knowledge that a person has consolidated through past experience. Performance on these sub-tests is highly correlated with amount of education, and tends not to decline with advancing age, or in response to frontal lobe injury. In contrast, measures of cognitive ability that rely less on assessment of consolidated knowledge and more on reasoning ability tend to be less sensitive to educational differences, and more sensitive to aging and frontal lobe dysfunction. Our primary objective in this study was to carefully test the hypothesis that individual variations in EEG and performance measures in the working memory task were related to cognitive ability per se. Thus, because of the considerations raised above, we further attempted to minimize variance in WAIS-R total scores that might be due to cultural or educational differences rather than cognitive ability by selecting a subset of the 80 participants who had only trivial differences between their verbal and nonverbal scores. This was accomplished by first taking the difference between the verbal and nonverbal cognitive ability scores for each subject and dividing it by his or her total score. Participants in the top (relatively high verbal scores) and bottom (relatively high nonverbal scores) quintiles of the distribution of the resulting variable had an average absolute difference between their verbal and nonverbal scores of 16.7 points (range 8 to 36). These extreme groups of participants were eliminated from initial analyses (they were compared in a secondary analysis described below). Across the original sample of participants, verbal and nonverbal sub-scores were correlated with an r=0.59 (p<0.01).

After eliminating the participants with the largest discrepancies between sub-scores, the verbal and nonverbal scores in the remainder of the sample (N=48) were much more highly correlated (r=0.91, p<0.0001). That is, variation in the WAIS-R scores of this subset of participants was likely to be primarily due to variation in general cognitive ability rather than individual differences in domain specific knowledge or skills.

Figure 4:
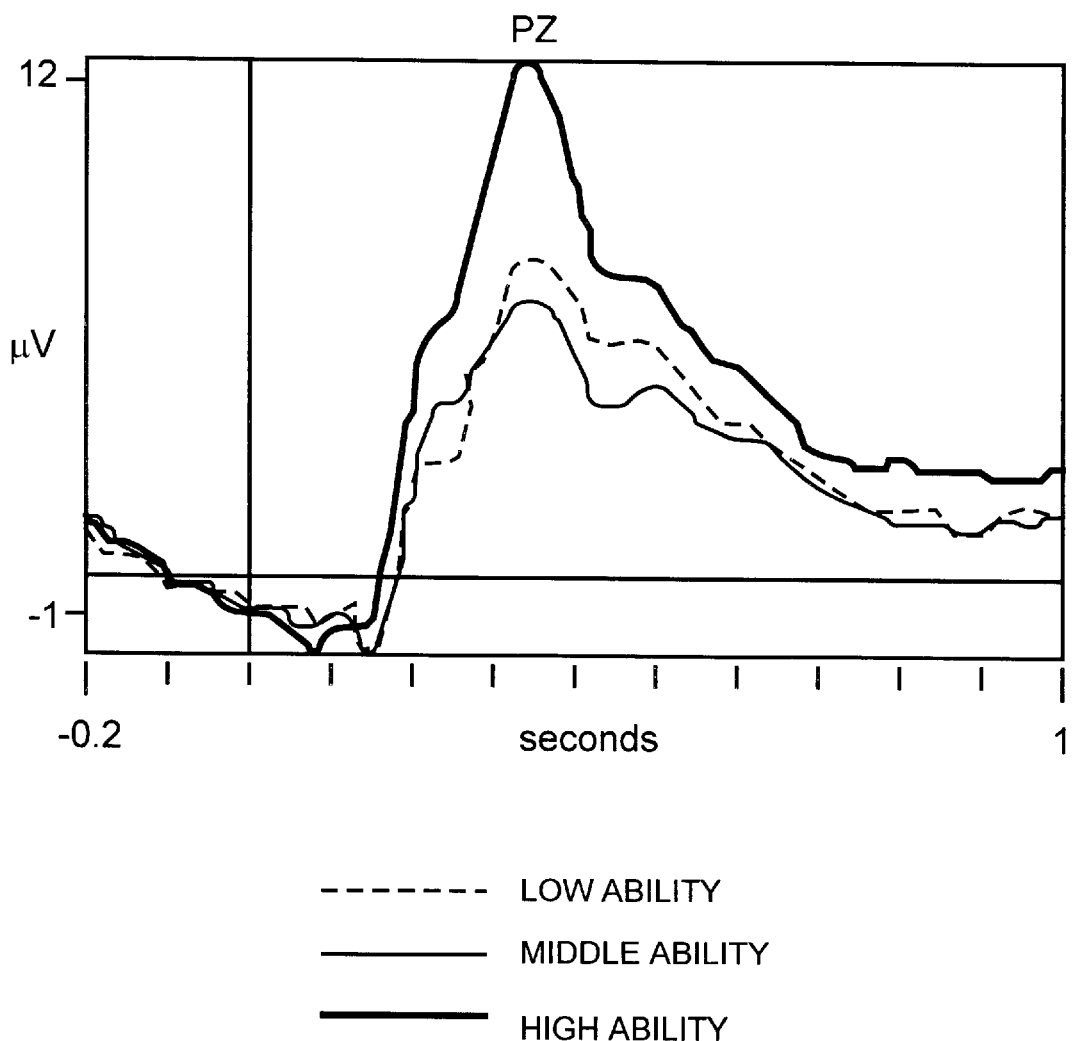
FIG. 4 is a graph showing the that the P300 evoked potential (EP or ERP) amplitude during the working memory task is larger in sixteen subjects with high cognitive ability (WAIS-R score=137), than in the same number of subjects with middle (WAIS-R score=127), or lower ((WAIS-R score=106) cognitive abilities. Since P300 amplitude indexes the subject's transient focused attention, this result shows that the high ability subjects were better able to focus attention on performing the task. This graph illustrates Experiment 1.
Figure 5:
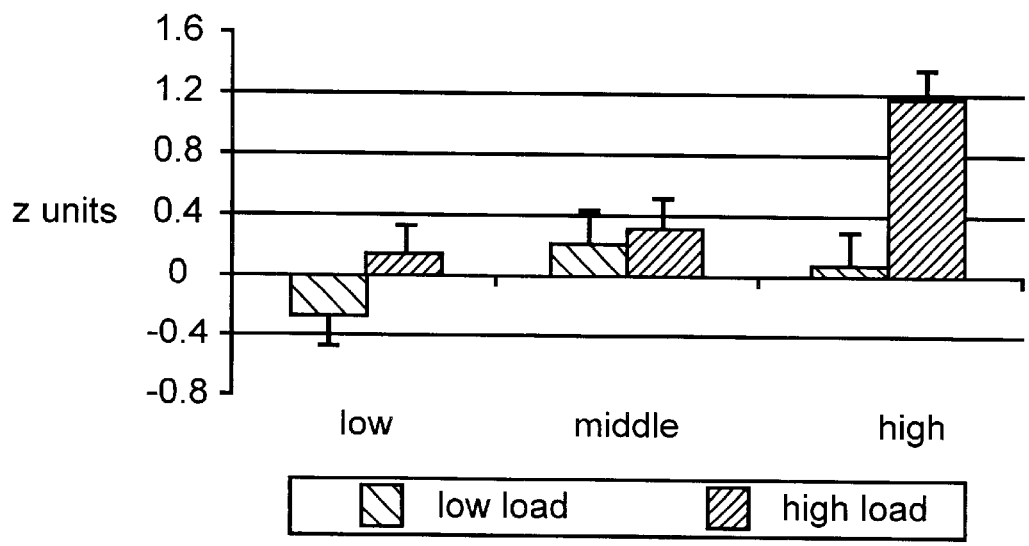
FIG. 5 is a graph showing that, for sixteen high cognitive ability subjects, frontal midline theta (frontal theta) power increases with practice, in the same session, of the high load (difficult) working memory task. Since frontal midline theta power increases when subjects make a sustained effort to keep attention focused on task performance, this result shows that high ability subjects made a greater effort to control attention in response to an increase in task demands than did the middle or low ability subjects. Furthermore, the high ability subjects' brains adapt more quickly to changes in mental workload imposed by the task. This graph illustrates Experiment 1.
Figure 6:
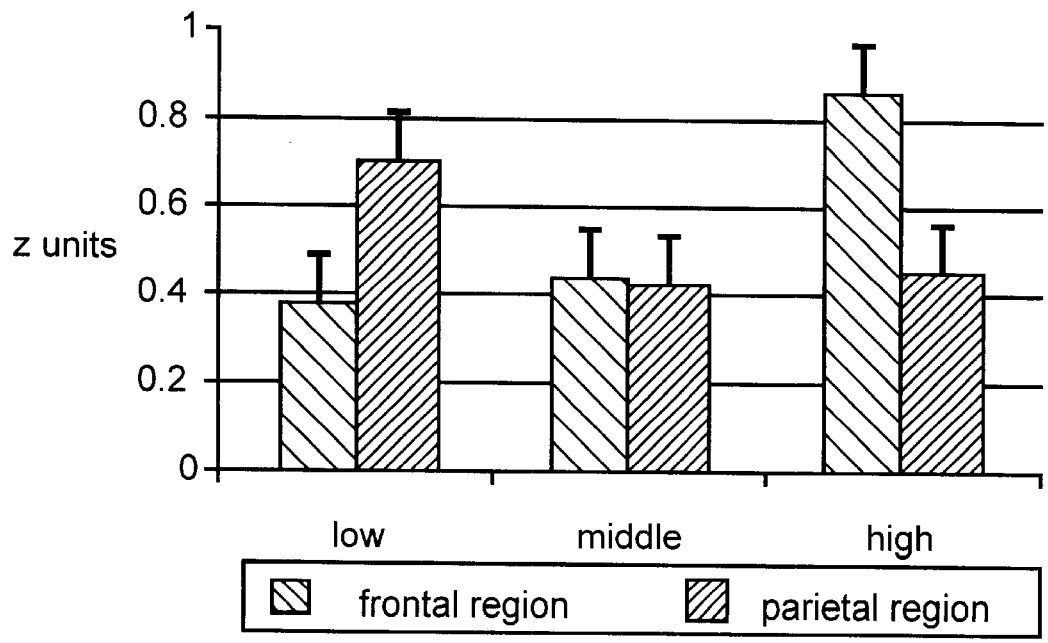
FIG. 6 is a graph showing that sixteen subjects with high cognitive ability have a larger practice-related increase in alpha power over the frontal region of the cerebral cortex, whereas sixteen subjects with lower cognitive ability have a larger practice-related increase in alpha power over the parietal region. Sixteen middle ability subjects displayed an approximately equal practice-related increase in alpha power over both frontal and parietal regions. Since alpha power is regionally attenuated when an area of cerebral cortex becomes engaged in task performance, this pattern of results suggests that high ability subjects tended to develop neurocognitive task performance strategies that relied more on parietal regions than on frontal regions. This graph illustrates Experiment 1.
Figure 7C:
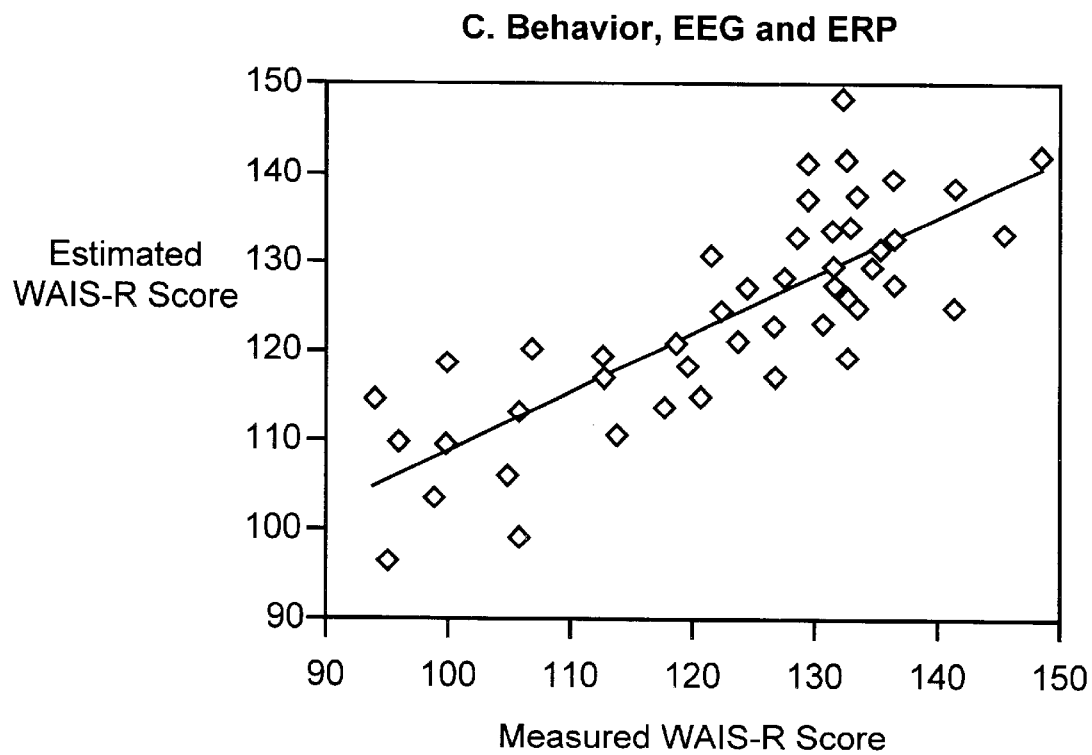
FIG. 7C is a graph showing stepwise multiple regression using a combination of eight behavioral and neurophysiological (EEG and ERP) variables to produce an estimate of test scores (vertical axis) that is more highly correlated (R=0.80) with scores on the Weschler Adult Intelligence Scale-Revised (horizontal axis) than that produced by the behavioral variables shown in FIG. 7A or the neurophysiological variables shown in FIG. 7B. This graph illustrates Experiment 1.

Results: Across these participants, average reaction time (RT) tended to be negatively correlated with WAIS-R scores, with the highest correlation in the low load task (r=−0.35, p<0.05). In contrast, accuracy, in terms of detectability of matching stimuli as measured by d', was positively correlated with WAIS-R scores, with the highest correlation in the high load task (r=0.30, p<0.05). Measures of neuroelectric signal magnitude tended to be positively correlated with WAIS-R total scores (FIGS. 4,5,6). Highest correlations were observed between test scores and the power of higher frequency (10–12 Hz) alpha signals recorded at a right inferior parietal electrode (P8) in the high load task ( r=0.38, p<0.01), and between test scores and amplitude of the P300 ERP Evoked Response Potential), elicited by correctly classified matching stimuli in the low load task (r=0.43, p<0.01). Past studies that have identified relationships between neurophysiological measures and intelligence test scores have been criticized for failing to utilize multivariate statistical methods to integrate both EEG and ERP measures into predictive functions. Thus, stepwise multiple regression was used to derive multivariate functions for predicting WAIS-R scores from combinations of task-related behavioral, EEG, alpha and ERP variables. These functions were derived from a set of measures that included first-order predictor variables indexing performance speed and accuracy, EEG alpha and theta power, and P300 ERP amplitude, and second order (derived) predictor variables indexing changes in the first-order measures between high-load and low-load task conditions or between left and right hemisphere or anterior and posterior electrode positions. All regression functions were limited to a maximum of 8 predictor variables in order to maintain a conservative 6:1 ratio of observations (participants) per variable. A stepwise analysis using only behavioral variables yielded an 8 variable function with a multiple R=0.56 ($R^2$=0.32, $F(8,39)$=2.27, $p<0.05$; FIG. 7A). An analogous analysis restricted to EEG and ERP variables yielded a function with a multiple R=0.73 ($R^2$=0.53, $F(8,39)$=5.59, $p<0.001$; FIG. 7B). When both behavioral and neuroelectric indices were included in the analysis, a multiple R=0.80 [$R^2$=0.64, $F(8,39)$=8.96, $p<0.0001$; FIG. 7C] was obtained. In this final analysis the stepwise selection procedure for entering variables led to the selection of variables from each category of observation made, including an accuracy and a RT measure, two measures of theta band EEG, three measures of alpha band EEG, and a P300 amplitude measure. That is, these different types of measures appeared to account for independent portions of the variance in predicting the WAIS-R scores. This latter combined function was submitted to a jackknife cross-validation analysis to test whether the findings would generalize to data not used for deriving the regression weights. In this analysis, 47 of the participants were used to derive the function weights, and the resulting equation was used to estimate the IQ test score of the remaining participant. This procedure was performed over 48 iterations so that each participant's score could be estimated as an independent test sample. This cross-validation analysis produced a correlation between the observed and estimated WAIS-R scores of R=0.71 ($R^2$=0.50, p 0.001), suggesting that the original regression equation would generalize well to a new sample of young adult subjects. A second set of analyses focused on the participants who were eliminated from the preceding analysis because they displayed relatively large differences between WAIS-R verbal and nonverbal sub-scores in one direction or the other. That is, for the two groups of participants (N=16 per group) whose test performance suggested that they have a "cognitive style" that is relatively verbal or relatively nonverbal, we sought to determine whether they also displayed differences with respect to their task related behavior and/or brain activity.

Figure 8:
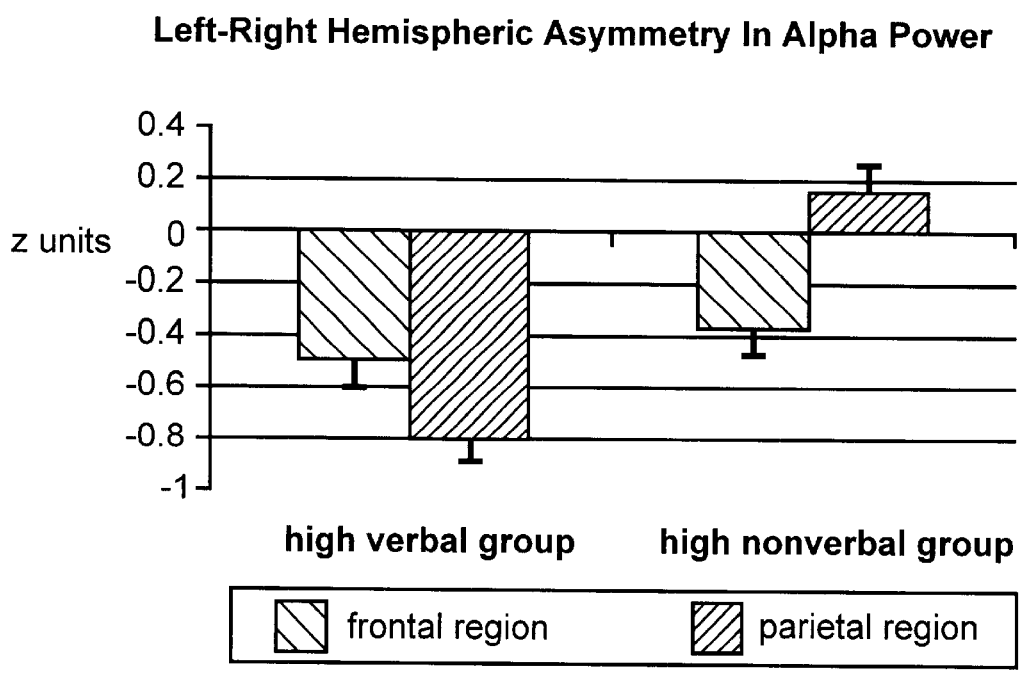
FIG. 8 is a graph showing differences in alpha power during the working memory task between the left and right frontal versus parietal cerebral cortical regions for high verbal and high nonverbal subjects with the same overall cognitive ability. Negative scores indicate relatively greater alpha power (less activation) over the right cerebral hemisphere. These results suggest that subjects with high verbal ability displayed a relatively large difference in task-related functional activation between the two hemispheres, with more activation of the left hemisphere. In contrast, high nonverbal subjects had a different neurocognitive strategy with relatively less asymmetry and relatively more activation of the right hemisphere especially over the parietal region. This graph illustrates Experiment 1.

No overall differences between the two groups were found in WAIS-R total score or in accuracy or RT measures on the working memory tasks. The groups did not differ in the absolute magnitude of the EEG power measures. However, they differed with respect to hemispheric asymmetries of alpha band signals (FIG. 8). More specifically, the high verbal ability group displayed a relatively large asymmetry in a at parietal electrodes, with a smaller signal over the left hemisphere. In contrast, the high nonverbal ability group displayed a relatively small asymmetry in the opposite direction, with a smaller alpha signal over the right parietal region ($F(1,30)$=8.9, $p<0.01$). This finding is consistent with prior reports that individuals might vary with respect to their characteristic asymmetry in hemispheric engagement during task performance.

In sum, the two extreme groups were equivalent in terms of their WAIS-R total scores as well as in their ability to perform the working memory task. However, neurophysiological measures suggest that they had different patterns of neural activation during task performance, perhaps reflecting differences in the strategies they employed. To determine whether these differences were sufficiently characteristic of the two groups to permit classification of individual participants into one group or the other, stepwise linear discriminant analysis was used to derive a classification function, and this classification function was cross-validated in a leave-out-one jackknife analysis. The final four-variable discriminant function thus derived included a measure of task-related parietal alpha asymmetry across the task conditions, measures of P300 amplitude to nonmatching trials in both high load and low load task conditions, and a measure of accuracy in the high load task condition. The original equation successfully classified 28/32 participants (87.5%); 27/32 participants (84.4%) were successfully classified in the cross validation analysis (binomial $p<0.001$ for both results).

Discussion: Together, the two analyses described above support the notion that the brain functions that support working memory are intimately related to individual differences in cognitive ability and cognitive style. In the first, we found that participants who had a relatively high WAIS-R total score tended to perform the working memory test faster and more accurately. They apparently were capable of achieving this higher level of task performance using relatively less of their overall cortical capacity as reflected in the positive correlation observed between WAIS-R scores and the amplitudes of the alpha rhythm and the P300 ERP. When combined into a multivariate function, such measures could be used to estimate overall IQ test scores with a high degree of accuracy. Furthermore, neurophysiological measures also differed between participants with a relatively high verbal aptitude and those with a relatively high nonverbal aptitude. Specifically, the alpha band results suggest that the participants with a relatively high nonverbal aptitude had greater activation of the right than the left parietal region during performance of the spatial working memory task, whereas this pattern of asymmetry was reversed for participants with a relatively high verbal aptitude. These differences were characteristic enough of the respective groups to permit highly significant statistical classification of individual participants into high verbal or high nonverbal cognitive style categories. This unambiguous evidence, obtained under strictly controlled experimental conditions, for the existence of a neurophysiological marker of individual differences in cognitive style, may help to clarify a controversy regarding hemispheric asymmetries in task-related EEG measures that was begun over twenty years ago (Gevins et al, 1979, 1980).

In effect, by recording the neural activity associated with a task requiring sustained attention and working memory, we have in a sense measured how much and what type of mental effort the participants expended to perform the task. The results indicate that the brain functions that support working memory are intimately related to cognitive ability and cognitive style, and they help to clarify the relationship between functional brain activation and complex cognitive functions.

These findings indicate that there is a close relationship between the factors that mediate performance on a standard psychometric test of cognitive ability and individual differences in neurobehavioral measures of working memory ability. The findings suggest that the superior task performance displayed by subjects with higher IQ scores is associated with differences in the magnitude and distribution of attention-related cortical activation. This implies that the individuals who excel at intellectually demanding activities might be those who are most able to intentionally concentrate and sustain attention on task requirements. The results also imply that the individuals with higher IQ scores make relatively more efficient use of their brain's resources in that they produce faster and more accurate responses with relatively less neuronal activation. Given the controversial nature of issues related to both cognitive abilities testing and the biological basis of intelligence, it is useful to clarify the societal implications of these results. First, unlike many psychometric tests of cognitive ability, the working memory tasks employed here could be performed without previous assimilation of any particular body of knowledge or set of intellectual skills. Thus, these data imply that it is possible to design a neurobehavioral measure of cognitive ability that is largely culturally neutral. Similarly, at least in the initial sample studied here, the index was insensitive to gender and ethnic differences among participants. The results do not address issues of heritability; a wide range of environmental factors might be expected to affect the type of index described here. Furthermore, a neurobehavioral index of cognitive ability does not imply that the cognitive ability of an individual is a fixed quantity. Indeed, such an index would likely be negatively impacted by any factor that interferes with cognitive function, including transient impairment produced by medications, alcohol, or fatigue, and more long-term impairment associated with chronic or progressive neurological disease. On the other hand, medical treatments to minimize or reverse the course of neurological disease, cognitive skills training, and early environmental enrichment, might have a positive impact on the index.

In sum, these results provide insight into the neural mechanisms underlying individual differences in higher order cognitive brain functions. The results demonstrate the feasibility of developing more effective and less ambiguous means of measuring human cognitive ability.

The following description is of an experiment that measured performance and neurological variables of the working memory task when subjects consumed diphenhydramine, caffeine, or alcohol, or stayed up all night, on separate occasions.

Method and Results of Experiment 2

Background: Many types of drugs are well known to affect mental acuity. Although a drug may be effective at treating its approved indication, it often has an undesirable side effect of diminishing mental acuity. Examples are the pain killing analgesics including the more classical narcotic based drugs such as those containing the narcotic codeine, as well as the more recently approved drugs such as bromfenac. Many of the currently prescribed muscle relaxants such as Flexeril are also widely reported to have effects on mental acuity. This is particularly the case in the earlier versions of the antihistamine type of drugs approved for human use. Examples of such drugs which have a long history of pharmaceutical use and are recognized by those expert in their effects to have the propensity to induce drowsiness are the diphenhydramines (e.g. Benadryl), clemastine (Tavist), brompheniramine (Dimetane), chlorpheniramine (Chlor-Trimeton), doxylamine (Unisom) and tripolidine (a component of Actifed and Sudahist). Antihistamines that are more recently approved for clinical and over the counter (OTC) use and furthermore are reported as having less drowsiness inducing properties are, for example, asternizole (Hismanal), loratadine (Claratin) and terfenadine (Seldane). In addition, it has been well recognized that the chronic drug therapy utilizing anticonvulsants for the control of seizure disorders can result in cognitive performance impairment. There are many other classes of drugs that are known to cause diminution of mental acuity, confusion, delirium and any other form of neurocognitive impairment as reported in the Physicians' Desk Reference, the drug manufacturer's product insert and in the published literature, for example "Worst Pills, Best Pills" Wolfe et al., Public Citizen's Health Research Group, 1993. These include anti-infective agents such as but not limited to antibiotics, systemically administered cortico steroids, and drugs used for the treatment of diabetes, gastrointestinal and cardiovascular problems (especially the beta-blockers; and diuretics). The more obvious classes of drugs that fall into this category of drugs that affect many aspects of neurocognitive functioning include the anti-depressants including the anxiolytics, the anti-psychotics, the barbiturates and other tranquilizers including sleeping aids. Alcohol and alcohol containing substances are also well recognized as being classical of this category of drugs. There are drugs that have the opposite effects to those discussed above, namely improving mental acuity, these would include the amphetamines, the nootropics and other memory enhancers as well as the obvious caffeine. Although there is little agreement on the actual magnitude of such induced deficits, there is general agreement as to the fact that a deficit does occur. In fact it may very well be the fact that it is the use of the conventionally utilized test methods themselves that give rise to the disparity in evaluation of the extent of the induced neurocognitive performance deficit. Thus, there is clearly an unmet need for a proficient, objective testing method to measure this ongoing demonstrable, if sometimes subtle, induced neurocognitive deficit.

As an example of desirable pharmacological action, as opposed to the unwanted side effects as described above, other drugs claim to either improve mental acuity or at least slow the progression of cognitive capabilities due to disorders such as age-related or other forms of dementia such as Alzheimer's disease. In this instance, there is a clear unmet clinical need for a sensitive, objective, easily repeatable neurocognitive test that can detect subtle improvement in cognitive performance and underlying neurophysiological processes while the patient, during the process of a clinical trial, is being treated with a drug awaiting marketing approval for the treatment of the aforementioned dementia disorders. The ability to monitor neurophysiological processes, in addition to performance of a cognitive task, provides the investigator with information about how the drug affects brain systems underlying cognitive performance. Such information is not available from psychometric tests that do not directly measure brain function. Frequently a non-drowsiness issue is raised with regard to an undesirable side effect with the administration of any of the above described classes of drug. The methods, as described in this specification, may be utilized to definitively evaluate the extent of the elicited change in mental acuity when a patient is taking an attention or higher mental acuity altering drug or even more importantly in a chronic situation. This would include the process of government sanctioned regulatory evaluation of the drug prior to approval for use in patients. As mentioned above there is no standardized, effective testing method currently used to assess the actual or suspected extent of changes in mental acuity that are associated with the described types of drug therapies. This lack of a clinically available standardized method for assessing the extent and ongoing progression of such neurocognitive effects has often been cited as a major confounding factor in the reported discrepancies between the results of different clinical trials of therapeutic intervention. In most cases, performance based on some ad hoc battery of behavioral tests of cognitive and psychomotor functions is employed. One of the inherent problems with such an approach is that such tests vary widely in their sensitivity to the mental parameters of interest. Consideration of the shortcomings of this practice typically led to the advocacy for the adoption of a particular battery of psychometric tasks as a clinical standard. However, even if a standard battery were universally adopted as the accepted norm, an important limitation of this approach would remain. Specifically, behavior can be seen as the end product of many neuro-functional subsystems. Because of arousal, motivational, or other factors well known to those expert in the art, an individual might fail to marshal the mental resources required for normal performance, and thus behavioral evidence might underestimate that person's true capabilities. Conversely, it is possible to temporarily mobilize the necessary mental resources to perform a task even when one is mildly debilitated, but such a temporary increment in performance may not accurately reflect a person's actual competence. Hence, such assessments based solely on behavior are limited in sensitivity and might fail to detect true and significant changes in mental status. An alternative and superior way of assessing neurocognitive impairment that alleviates the problems associated with currently available methods of neurocognitive evaluation forms the basis of the current invention.

This study was designed to determine the sensitivity of performance and task-related EEG measures to changes in a subject's neurocognitive state due to fatigue, or to the ingestion of common substances such as alcohol, caffeine, or drowsiness-inducing antihistamines. The impact of these factors on performance and EEG measures was assessed while subjects performed easy and difficult versions of a working memory task. Previous research has shown that the performance of this working memory task is associated with characteristic modulation of the ongoing EEG, and that these changes are related to task difficulty in a systematic manner. For example, signal power in the upper theta band (5–7 Hz) over midline frontal cortex increases as task difficulty increases (Gevins et al 1998, 1997). This signal appears to be generated in the region of the anterior cingulate cortex, an important component of a frontal brain circuit involved with attention. Conversely, signal power in the slow (8–10 Hz) and fast (10–12 Hz) alpha bands over posterior cortex decreases as task difficulty increases. The alpha rhythm seems to represent a type of "cortical idling: as the proportion of neurons activated by a task increases, the alpha rhythm decreases. Changes in the alpha rhythm can thus be used to infer the regions and proportions of cortex involved in task performance. We expect that factors that affect a subject's cognitive abilities, such as fatigue, alcohol, drowsiness-inducing antihistamines and caffeine will produce systematic changes in these electrophysiological signals of cognition, and will provide important information on a subject's cognitive status that cannot be obtained from behavioral measures alone.

Method

Sixteen healthy adult subjects (21–32 years, mean age 26 years, 8 females) were trained on the working memory tasks (FIG. 2) prior to beginning the experiment. After training, all subjects participated in 5 sessions, separated from each other by at least one week. One session involved recording from subjects while they remained awake over night; the others involved recording from subjects after they had ingested alcohol, caffeine, antihistamine or a placebo.

The four drug sessions were conducted according to a fully counterbalanced, placebo-controlled, double-blind design. In each session subjects consumed two pills (unmarked gelatin capsules) and a mixed drink. The pills contained either 50 mg of the antihistamine diphenhydramine (active ingredient in Benadryl), 200-mg of caffeine (equivalent to 2 cups of coffee), or a placebo consisting of powdered sugar. The pills were given with a 500 cc drink containing either 0.88g/kg 95% ethanol mixed in fruit juice (this produced an average peak blood alcohol content (BAC) of 0.08), or containing 495 cc of fruit juice with 5 cc of alcohol floated on top to mimic the smell and taste of the drink. Neither the subject nor the experimenter knew which drug condition was administered in any session. A third party, not otherwise involved in the experiment administered the drugs and recorded the Breathalyzer readings obtained at the beginning of each recording interval within each session.

Each of the four drug sessions involved a baseline recording, followed by drug administration. In each session, subjects then participated in four post-drug recording intervals, each lasting approximately 40 minutes. The first interval began 0.5 hrs after drug consumption; the remaining three intervals began at hourly intervals thereafter. A Breathalyzer test was administered at the beginning of each interval, followed by subjective sleepiness rating scales. Task-related EEG was then recorded while subjects performed the easy and difficult versions of the WM task. EEG was also recorded in each interval while subjects rested quietly with their eyes open and with their eyes closed.

In the overnight session, subjects arrived in the laboratory in the early evening, were prepared for the EEG recording, and then participated in five 40-minute recording intervals throughout the night. The first interval occurred at 11:00 PM, the second at 12:30 AM, the third at 1:30 AM, the fourth at 3:30 AM and the fifth at 5:00 AM. Within each interval, subjects completed subjective sleepiness rating scales, had their EEG recorded while performing easy and difficult versions of the working memory task, and had their EEG recorded while they rested quietly with their eyes open and closed. In the intervals between recording blocks, subjects performed repetitive computer tasks to help induce fatigue.

EEG was continuously recorded from 28 scalp electrodes using a linked-mastoids reference. Physiological signals were band-pass filtered at 0.01 to 100 Hz and sampled at 256 Hz. Automated artifact detection was followed by application of adaptive eye movement contaminant removal filters. The data were then visually inspected and data segments containing possible residual artifacts were eliminated from subsequent analyses.

Evoked potentials (EPs) were computed by averaging the EEG beginning 0.2 seconds prior to stimulus onset to 1.0 seconds afterwards. The EPs were low-pass filtered at 20 Hz. EP amplitudes were measured with respect to the average amplitude in the 0.2 second baseline period before stimulus onset. To obtain measurements of EEG power in different frequency bands, Fast Fourier transforms were computed on 50% overlapped, 512 sample Hanning windows for all artifact-free trials. Average power spectra were then normalized with a 10-dB log transform. Repeated measures analyses of variance were used to determine the effect of each manipulation on the individual performance and neurophysiological variables.

Group stepwise, linear discriminant analyses were then performed to determine how well three types of indices could discriminate each drug condition from the placebo condition. For the *Behavioral Index,* only behavioral variables were submitted as features in the analysis. For the *Neurophysiological Attentional* index, task-related EEG and EP features were used as variables. For the *Neurophysiological* Alertness index, neurophysiological variables known to fluctuate with Alertness were used. In all cases, the discriminant equations were restricted to a maximum of four features each.

For each index type, a two-step process was used to analyze the data from each drug session. First, data from all the post-drug intervals were submitted to a step-wise Linear Discriminant Analysis (LDA) to discriminate between drug and placebo conditions. The features chosen in this analysis (restricted to a maximum of four) were then submitted together to a LDA to discriminate drug from placebo data in each interval (including the baseline interval). These LDAs were performed using a cross-validation, leave-out-one jack-knife approach. Only the cross-validation results are reported here.

For the overnight data, a stepwise LDA was used to discriminate data obtained in the drug session baseline intervals (which occurred in the morning or early afternoon) from data obtained in the fifth overnight interval (occurring at 5:00 AM). The equation obtained from this analysis was then applied to data obtained from the remaining four overnight intervals. The cross-validation results are reported for the drug-session baseline interval and the last overnight interval (5:00 AM).

Results

Alcohol. BAC peaked, on average, at 0.08 during the first post-drug interval and decreased to an average of 0.04 by the end of the fourth post drug interval (4.5 hours after drinking). Alcohol produced minor effects on the performance of the working memory tasks. It did not significantly affect response accuracy but did affect reaction time ($p<0.05$): Relative to the placebo condition, alcohol produced quicker responses in the difficult task and slower responses in the easy task. Alcohol dramatically affected many neurophysiological variables. Relative to the placebo condition, alcohol produced an increase in frontal alpha ($p<0.001$), slow posterior alpha ($p<0.001$), posterior theta ($p<0.001$), and slow beta power ($p<0.001$). It also significantly increased the power of the frontal midline theta signal ($p<0.001$), and attenuated the difference between the difficult and easy task typically observed in this signal (Task Difficulty by Drug interaction $p<0.01$).

Figure 9:
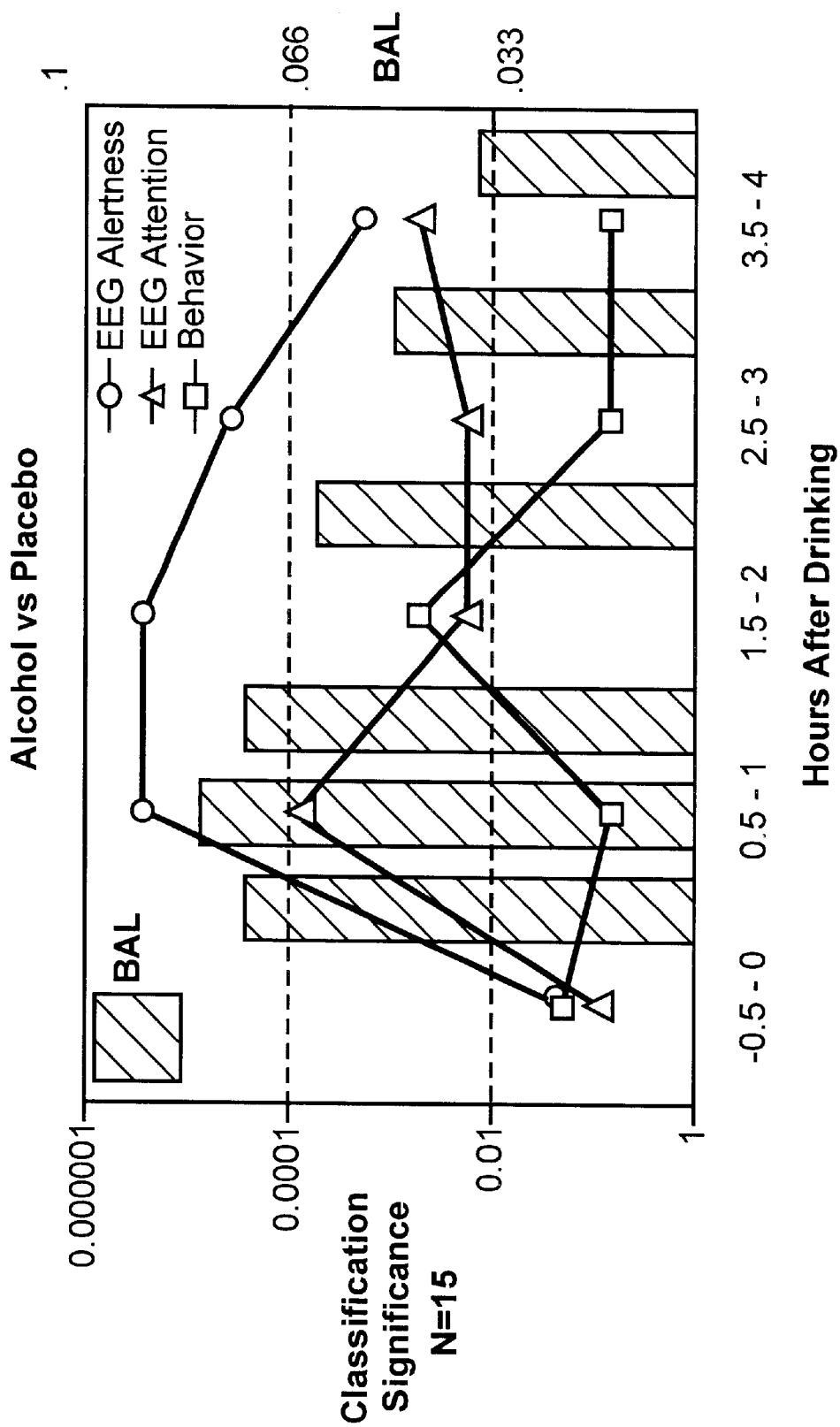
FIG. 9. is a graph which charts, on the X axis, the time post drug consumption and on the Y axis the significance of classification for the Alcohol vs. Placebo linear discriminant analysis for the Behavioral Index, the Neurophysiological Attentional Index and the Neurophysiological Alertness Index. This graph illustrates Experiment 2. Results above 0.01 are considered significant.

The results of the LDAs discriminating alcohol states from placebo states are shown in FIG. 9. The Neurophysiological Alertness Index used two alpha-related measures (the ratio of theta to alpha power over occipital channels, and the difference in fast alpha power over occipital channels between eyes open and eyes closed states) and two EP measures (N1 amplitude and N1 latency). The Neurophysiological Attentional Index used three EP features (relating to the P200 and P300 components) and one EEG feature, (the difference in fast alpha power between the resting, eyes open state and the performance of the easy WM task). The Behavioral Index used two behavioral features (the ratio of reaction time to accuracy in the easy task, and reaction time variability in the difficult task). Of the three, the Neurophysiological Alertness Index produced the best discrimination between alcohol and placebo states. This index showed peak discrimination during the first post-drinking interval; the interval in which the BAC was the highest. It also showed significant discrimination for the remaining three post-drug intervals. The Neurophysiological Attentional Index showed significant discrimination between placebo and alcohol states in all intervals. Peak discrimination occurred in the first post-drinking interval (0.5–1 hours after drinking). The Behavioral Index showed significant discrimination in the second post-drinking interval (1.5–2 hours after drinking), and chance levels of classification in all other intervals.

These results show that alcohol produces discernible changes in alertness and attentional-abilities before any changes in behavior are observed. They also suggest that subjects maintained a high level of performance on the task at the cost of increased attentional efforts.

Figure 10:
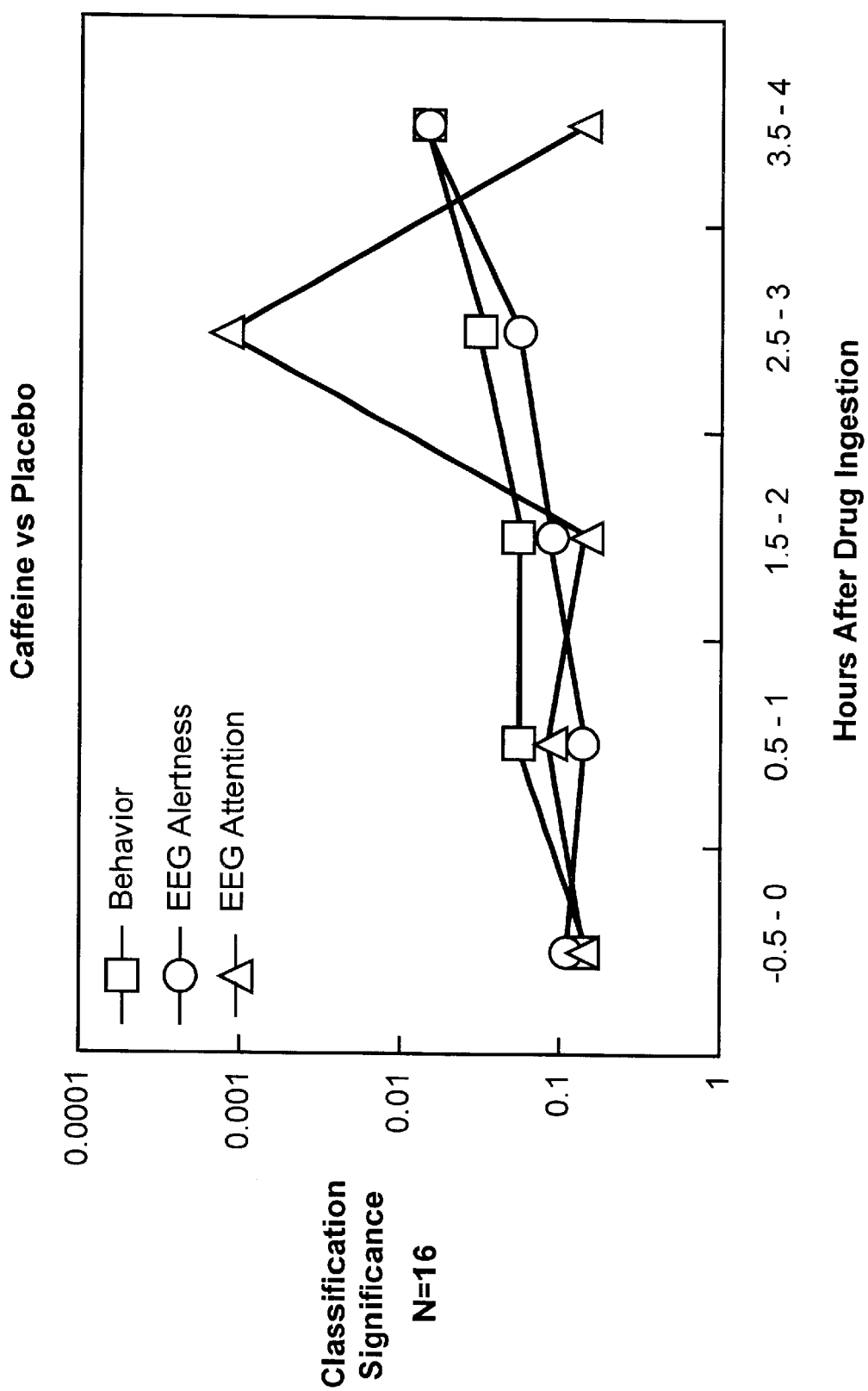
FIG. 10 is a graph which charts, on the X axis, the time post drug consumption and on the Y axis the significance of classification for the Caffeine vs. Placebo linear discriminant analysis for the Behavioral Index, the Neurophysiological Attentional Index and the Neurophysiological Alertness Index. This graph illustrates Experiment 2. Results above 0.01 are considered significant.

Caffeine. Caffeine showed modest behavioral and EEG effects. Relative to the placebo condition, caffeine significantly improved response accuracy ($p<0.05$) but did not significantly affect reaction time in the working memory tasks. Relative to the placebo condition, caffeine significantly decreased the power in several EEG bands, including posterior theta ($p<0.001$), slow ($p<0.001$) and fast ($p<0.01$) alpha, and slow ($p<0.001$) and fast ($p<0.05$) beta. In the LDA (FIG. 10) neither the Behavioral Index, which used a single behavioral feature (reaction time variability in the difficult task), nor the Neurophysiological Alertness Index, which used two EEG features (the ratio of theta to alpha power over occipital channels, and delta power over occipital channels in the resting, eyes open state), showed significant discrimination in any interval. Only the Neurophysiological Attentional Index was able to significantly discriminate between the two states. This index, which used two EEG features (the difference in frontal midline theta power between the easy and difficult task, and the difference in slow alpha power between the resting, eyes open state and performance of the easy task) showed significant discrimination in the third post-drug interval (2.5–3 hours after drug ingestion). These results indicate that at the dosage given caffeine affects the neurophysiological networks of attention in the brain although it produces only subtle effects on task performance.

Diphenhydramine. Diphenhydramine significantly impaired performance on the working memory task: responses were significantly slower ($p<0.001$) and less accurate ($p<0.001$) than in the placebo condition. Diphenhydramine also produced a number of changes in the EEG. Compared with the placebo condition, diphenhydramine decreased the frontal midline theta signal in the difficult task ($p<0.05$), and thus attenuated the task difficulty effect normally observed in this signal (Task Difficulty by Drug interaction $p<0.05$). It also increased posterior theta activity ($p<0.05$) and increased slow ($p<0.01$) and fast ($p<0.001$) beta activity. Diphenhydramine produced smaller N100 ($p<0.01$) and P200 ($p<0.05$) responses compared with the placebo condition.

Figure 11:
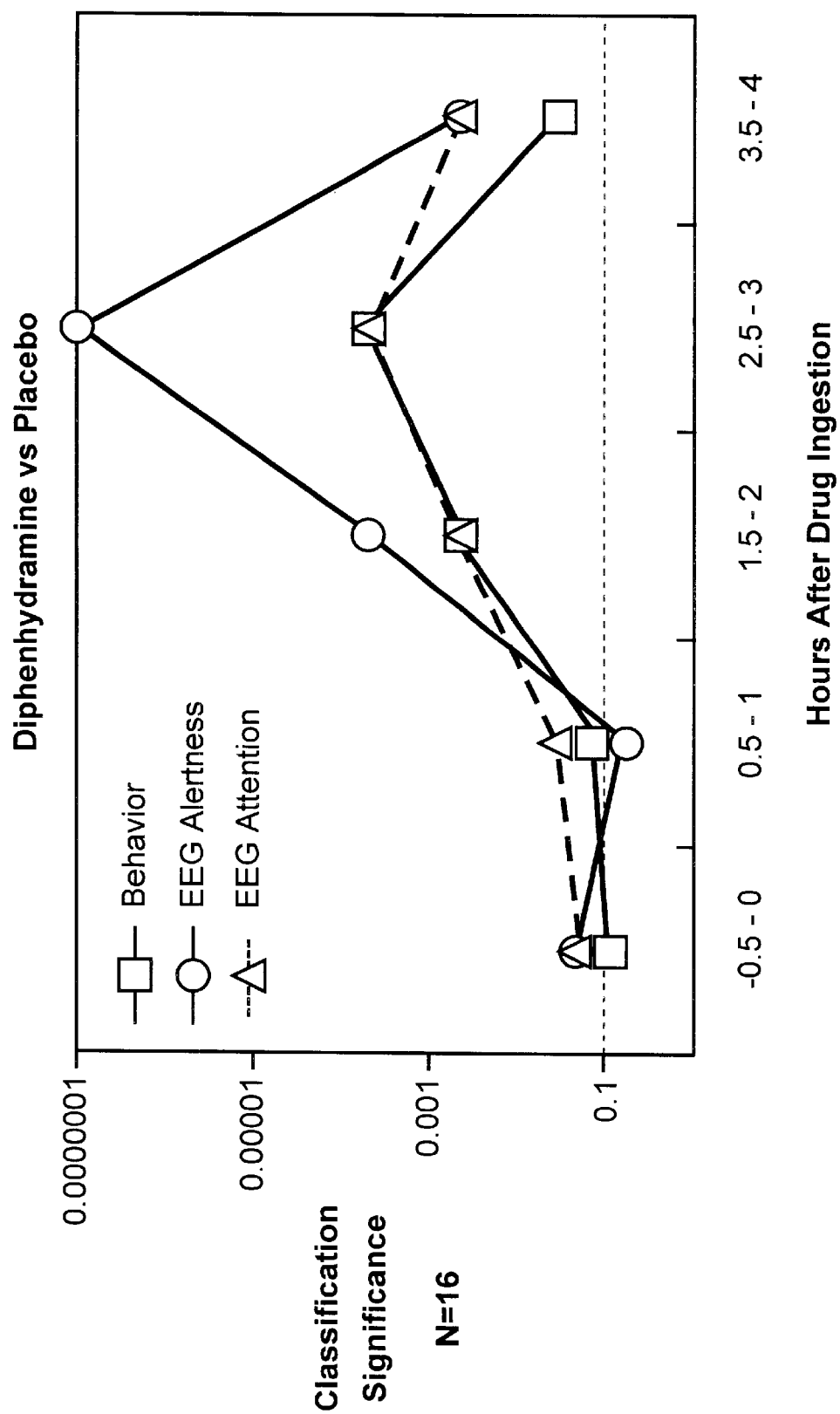
FIG. 11 is a graph which charts, on the X axis, the time post drug consumption and on the Y axis the significance of classification for the Diphenhydramine vs. Placebo linear discriminant analysis for the Behavioral Index, the Neurophysiological Attentional Index and the Neurophysiological Alertness Index. This graph illustrates Experiment 2. Results above 0.01 are considered significant.

The Neurophysiological Alertness Index (FIG. 11) used four features (slow horizontal eye movements measured by frontal EEG delta power, the ratio of theta to alpha power over occipital channels, the difference in fast alpha power over occipital channels between eyes open and eyes closed states, and delta power over occipital channel in resting eyes open state). This index performed better than the other two indices at discriminating between the drug condition and the placebo condition. It produced significant classification in all but the first post-drug interval, and showed the highest classification during the third post-drug interval (2.5–3 hours after drug ingestion). The Behavioral Index, which used two variables (reaction time variability in the easy task, and response accuracy in the difficult task), showed significant classification only in the second and third post-drug intervals, with peak discrimination occurring in the third post drug interval. Classification accuracy returned towards chance levels of discrimination in the final post-drug interval (3.5–4 hours after drug ingestion). The Neurophysiological Attentional index used three EEG variables (the difference in frontal midline theta power between the easy and difficult task, the difference in slow alpha power between the resting, eyes open state and performance of the difficult task, and the hemispheric asymmetry in the task-difficulty modulation of the fast alpha signal over the parieto-temporal-occipital junction area.). This index showed the same pattern of discrimination as the behavioral Index throughout the session, except for the final post-drug interval (3.5–4 hours post drug ingestion). The Neurophysiological Attentional index showed significant classification during this interval but the Behavioral Index did not. These results suggest that diphenhydramine has a large fatigue-inducing effect that produces the greatest impairment 2.5 to 3 hours after drug ingestion. The similar functions for the neurophysiological attention-related index and the behavioral index suggest that subjects did not increase their effortful concentration on the task sufficiently to overcome the drowsiness-inducing effect of the drug to maintain performance. However, the Neurophysiological Attentional Index did show significant discrimination in the final post drug interval, at a time when performance returned to near baseline levels. This suggests that the level of performance achieved in this interval came at the cost of increased mental effort necessary to combat the lingering effects of the drug.

Figure 12:
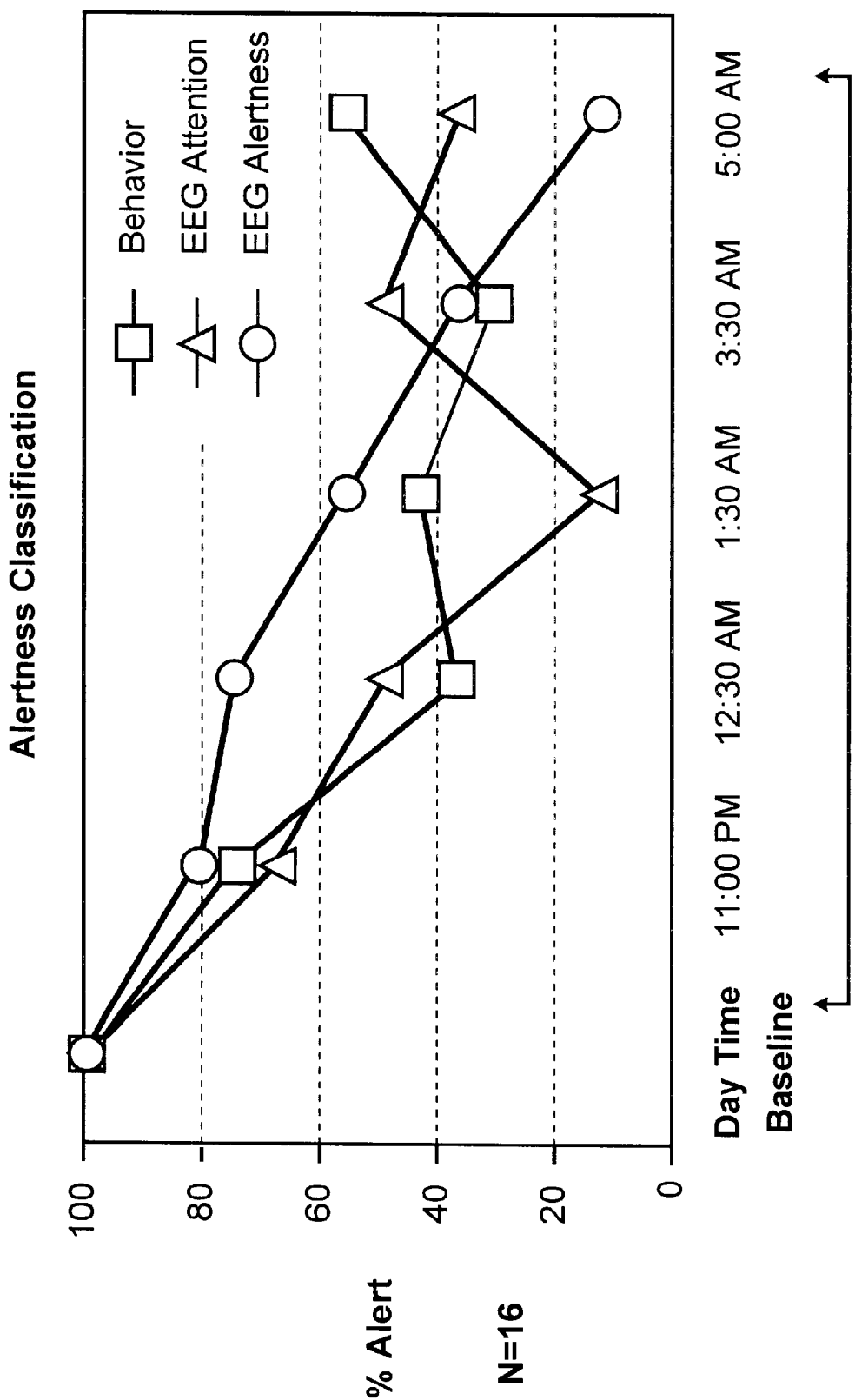
FIG. 12. is a graph which charts, on the X axis, the time of day, and on the Y axis, the percentage of subjects classified as sleepy for the Behavioral Index, the Neurophysiological Attentional Index and the Neurophysiological Alertness Index. This graph illustrates Experiment 2.

Fatigue. The requirement to remain awake overnight had a detrimental effect on task performance. Responses were significantly slower ($p<0.01$) and less accurate ($p<0.05$) at the end of the session (5:00 AM) than at the beginning of the session (11:00 PM). Subjective ratings indicated that subjects felt increasingly sleepy throughout the night. Fatigue produced several changes in the EEG, including producing an increase in slow alpha ($p<0.01$) activity, and slow ($p<0.001$) and fast ($p<0.001$) beta activity. Fatigue also significantly decreased the N100 ($p<0.001$), P200 ($p<0.05$) and P300 ($p<0.01$) responses. For each index type, a stepwise LDA was performed to discriminate between "Alert" (daytime baseline) and "Sleepy" (5:00 AM) states. This equation was then applied to data from the remaining overnight intervals to classify subjects as "Alert" or "Sleepy". The percentage of subjects classified as Sleepy by each index is shown in FIG. 12 (the cross-validation results are shown for the Day Time baseline and 5:00 AM session). The Neurophysiological Alertness Index consisted of two features (slow eye movements and delta power over occipital channels in the resting eyes open state). This index classified all subjects as alert in the afternoon baseline interval, and the majority of subjects (14/16) as sleepy in the 5:00 AM interval. There was a steady rise in the number of subjects classified as sleepy from the day time baseline interval to the 5:00 AM interval. The Behavioral Index, consisted of a single variable (reaction time in the difficult task). It showed significant classification in the Day Time baseline interval, classifying all but three subjects as Alert. The percentage of subjects classified as sleepy on the basis of this index increased steadily from the day time intervals until the 12:30 AM interval. Most subjects are classified as sleepy on the basis of this Index until the 5:00 AM session. In this final session, fewer subjects are classified as Sleepy than in the previous early morning intervals. The Neurophysiological Attentional Index consisted of one EP variable (P300 amplitude) and three EEG variables (the task difficulty difference in frontal midline theta power, the difference in slow alpha power between the resting eyes open state and performance of the easy task, and the hemispheric asymmetry of slow alpha over central cortex in the difficult task). The results of this index are similar to those of the Behavioral Index. However, at the 5:00 AM session, where the Behavioral Index shows a decrease in the percentage classified as Sleepy, the Attentional Index shows an increase. This, combined with the results of the Alertness Index, indicate that the improvement in performance seen in the last session is not due to an increase in Alertness, but to an increase in attentional effort.

Conclusions

These results demonstrate that both task-related and resting EEG data are sensitive to common factors that affect concentration, such as fatigue, or the consumption of alcohol, drowsiness-inducing antihistamines, or caffeine. In this study, we compared the ability of behavioral indices to discriminate between drug and placebo states (and between alert and sleepy states) to the ability of neurophysiological indices to discriminate between these states. The results showed that neurophysiological measures of Alertness and attention provide important additional information about a subject's cognitive state than can be derived from behavioral measures alone.

Alcohol consumption, sufficient to raise the BAC to 0.08, produced minor effects on behavioral performance, but produced clear effects in neurophysiological measures related to alertness and attention. Both the Alertness and Attentional Neurophysiological Indices discriminated between alcohol and placebo states at an earlier point in time than did the Behavioral Index. This suggests that neurophysiological variables could be used as important leading indicators of impending performance degradation. Additionally, the better between-state discriminability of the Neurophysiological Attentional Index relative to that of the Behavioral Index suggests that subjects compensated for the effects of alcohol by altering their attentional strategy, perhaps by increasing mental effort. An examination of behavioral features only could lead to the conclusion that alcohol does not affect cognitive ability in the performance of this task. However, the changes in the neurophysiological features related to attention show that it does.

In the overnight data, subjects showed a small improvement in performance during the last interval compared with the prior early-morning intervals. This could indicate an increase in Alertness due to circadian fluctuations, however, the neurophysiological measures of Alertness argue against this interpretation. In contrast to the Behavioral Index, the Neurophysiological Attentional Index shows an improvement in discrimination during this interval. This suggests that the observed improvement in performance was likely due to an increase in effort-perhaps motivated by the knowledge that this was the last interval in the long overnight session.

Similarly in the diphenhydramine session, there was a dissociation between the results of the Behavioral Index and those of the two neurophysiological indices in the final interval. In this dataset, the neurophysiological Alertness Index showed a dramatic difference between placebo and drug states. Correspondingly, task performance was significantly compromised. The Attentional Index showed the same pattern of results as the Behavioral Index until the final interval. In this interval, both the Alertness Index and the Attentional Index showed significant discrimination between states, but the Behavioral Index did not. This again argues for an "end of session" effect in which behavior improves as the cost of increased neurophysiological effort.

This study examined four separate conditions in which stressors caused alterations in cognitive ability. In all cases, the neurophysiological measures provided important additional information to aid in the interpretation of the behavioral results.

The following is a description of a pilot experiment in which subjects received alprazolam, a commonly prescribed anti-anxiety medication.

Method and Results of Experiment 3

Method and Procedure: The alprazolam study is designed to determine the dose-response effects of a commonly prescribed anti-anxiety medication on EEG indices of attention and alertness. On five separate drug intervention days, subjects will be assessed before and after ingesting different doses of alprazolam, a triazolobenzodiazepine better known by the brand name Xanax that is used for the treatment of anxiety disorders and panic attacks. The original protocol specified that subjects would ingest a placebo (sugar pill), low (0.125 mg), moderate (0.25 mg), or high (0.50 mg) dose of alprazolam on different experimental days, with the moderate dose being repeated on a fifth day to assess test-retest reliability.

Prior to beginning this placebo-controlled, double blind experiment, a small pilot study was conducted in which 3 members of the research staff participated in a total of 5 experimental sessions, and performed 0-back and 2-back spatial working memory tasks, and eyes open and closed resting EEG conditions. Subjective effects were measured with our Drug Effects Scale and the Karolinska and Stanford Sleepiness Scales. The baseline session was followed by drug administration, which in turn was followed by three 1 hour post-drug sessions. Two subjects originally piloted the moderate (0.25 mg) dose, and their subjective reports and behavioral results indicated that this dose did not have a strong effect. Three subjects (including the original two) then piloted the high (0.5 mg) dose. No placebos were given, and drug condition was not conducted blindly.

Figure 13:
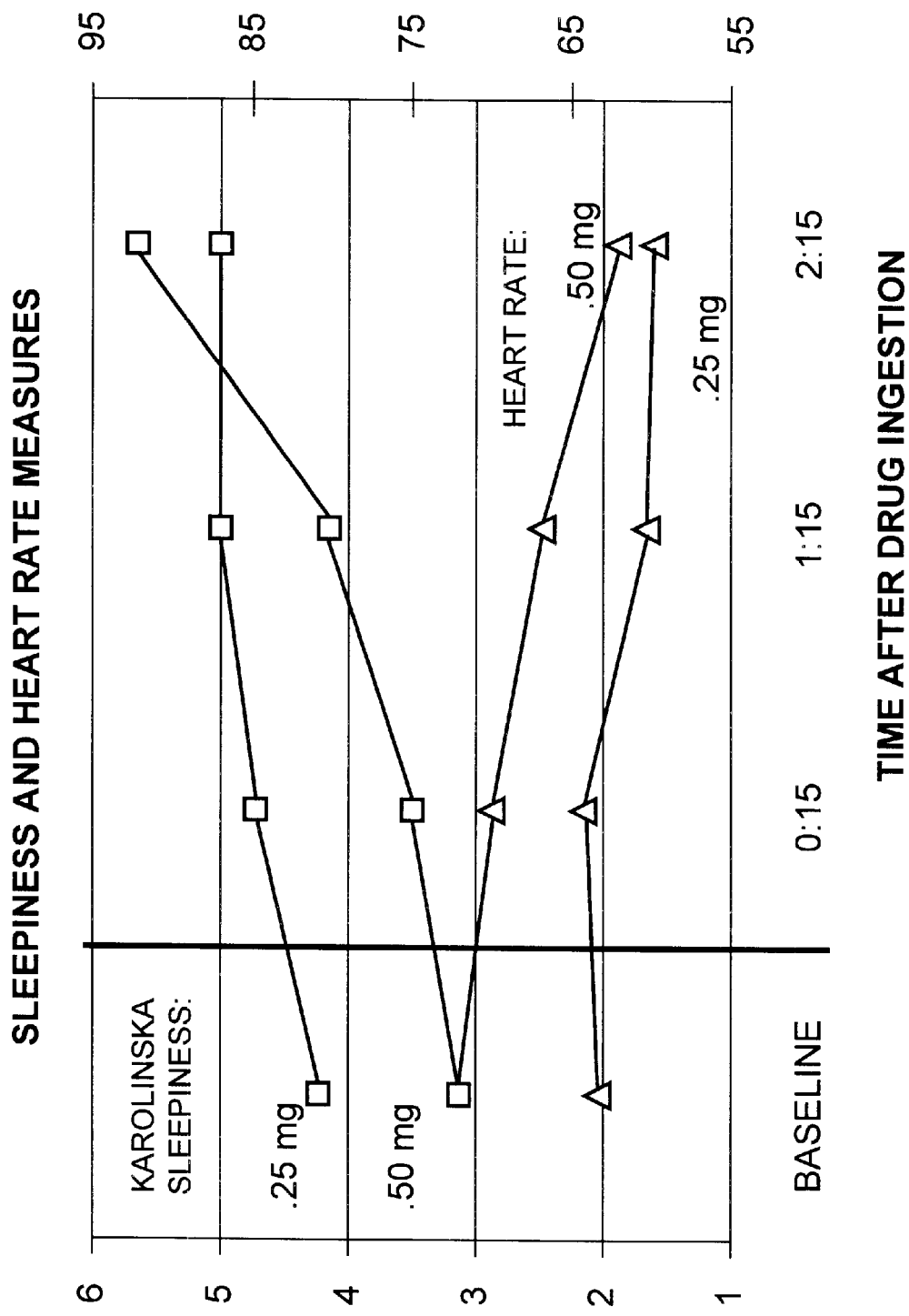
FIG. 13 is a graph showing Karolinska Sleepiness Scale ratings (upper 2 lines; left y-axis) and Heart Rate measures (lower 2 lines; right y-axis) in the 0.25 and 0.50 mg alprazolam dose conditions. This graph illustrates Experiment 3.

Results: Because of the small number of subjects in the pilot study, the following results can not be statistically assessed and should be viewed as merely descriptive. Both doses had their largest effects in the last post-drug session, 2–3 hours after ingestion, although EEG data suggest that the 0.25 mg effects were waning by that time. The 0.5 mg of dose of alprazolam produced noticeable physiological and subjective effects, as heart rate decreased and ratings of sleepiness and "druggedness" increased throughout the session. The 0.25 mg dose produced smaller effects in the same direction. Sleepiness and heart rate data are presented in FIG. 13. Behavioral effects were small, as RT and error rate in the WM task increased slightly after both doses, with no apparent drug/load interaction.

Figure 14:
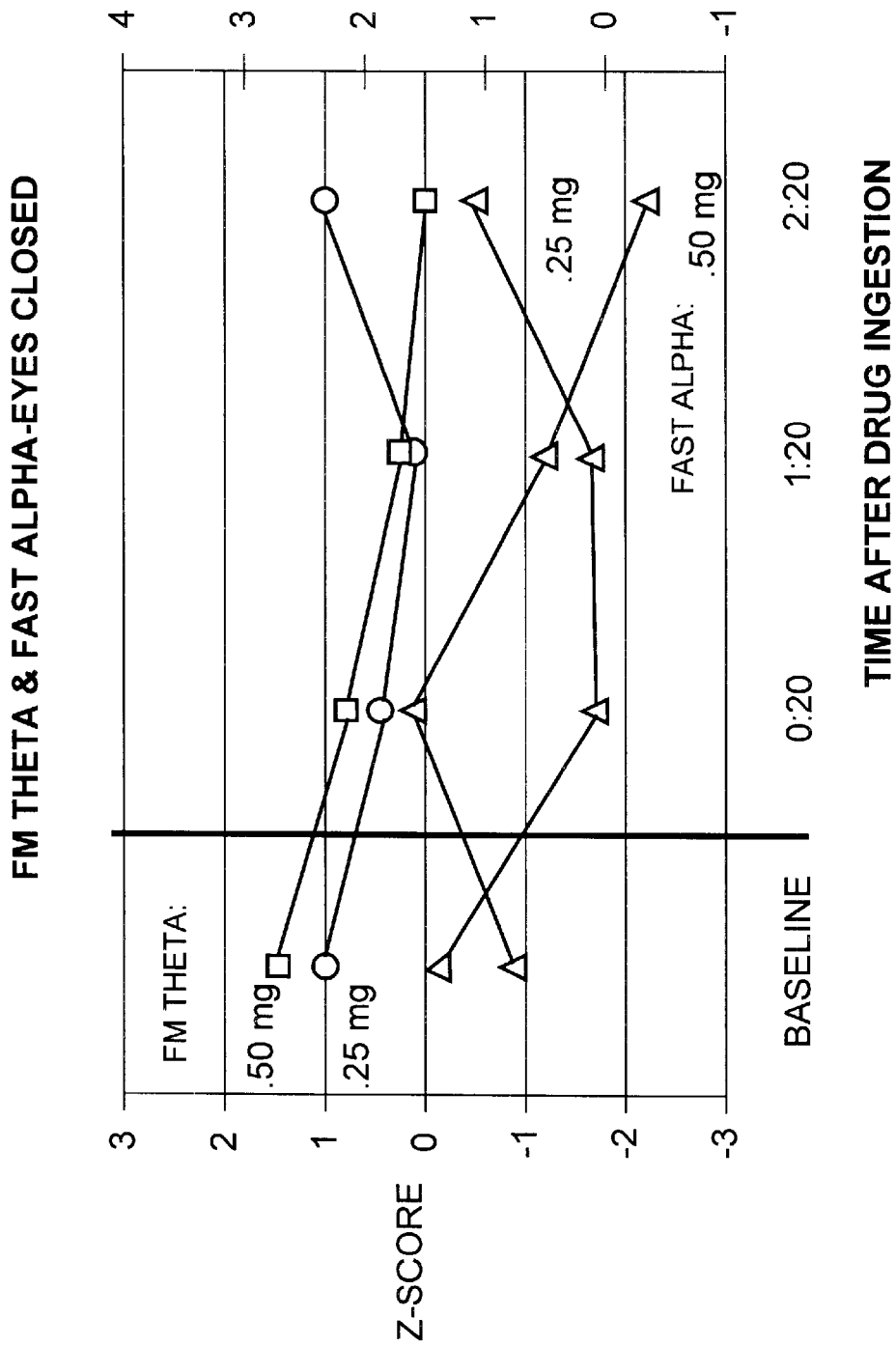
FIG. 14 is a graph showing Frontal Midline Theta at aFz (upper 2 lines; left y-axis) and Fast Alpha at Oz (lower 2 lines; right y-axis) from the eyes closed resting blocks in the 0.25 and 0.50 mg alprazolam dose conditions. Scores were standardized across eyes closed and eyes open (not pictured) blocks. This graph illustrates Experiment 3.

The EEG results suggest that alprazolam produced a decrease in theta at both anterior and posterior electrode sites (FIG. 14). This decrease was more marked in the 0.50 mg that the 0.25 mg dose condition. Fast alpha features also decreased in the eyes closed resting condition. Peak Beta at Cz increased after the 0.50 mg dose but was unaffected by the 0.25 mg dose. P300 amplitude decreased after alprazolam, more so in the high than the low load condition. P300 latency was not reliably affected by the drug. Further analysis is required to fully understand the pilot results. However, subjective reports and a review of the literature suggests that 0.5 mg is a moderate rather than a high dose of alprazolam, and that the formal study should employ low, moderate, and high doses of 0.25, 0.5, and 1.0 mg, respectively, to show clearer dose-response effects.

Modifications may be made in the present invention within the scope of the subjoined claims. For example, the method may include the steps of (a) presenting an attention demanding task and a resting control condition to the subject and, simultaneously, (b) measuring the subject's behavioral responses to the task, i.e., the subject pushing a button and (c) the subject's neuroelectric activity, using EEG in a computer, (d) comparing the subject's responses with a normal group or with the subject's own prior measurements, and (e) displaying the subject's overall cognitive ability or changes in the subject's cognitive ability, for example, due to medicine, a remedial program or the passage of time. The steps (a)–(c) may be performed to obtain a baseline score and then repeated to obtain another score, which is compared to the baseline score or compared to a series of prior scores.

The subject's neural activity is measured while performing the attention-demanding task to determine one, or more, of the group selected from:

(i) characterizing the subject's level of alertness by EEG measurement of the subject's frontal delta power associated with slow horizontal eye movements, posterior theta and delta power, and ratios of posterior theta to alpha and delta to alpha powers;

(ii) characterizing the subject's mental effort and brain utilization by EEG measurement of the subject's parietal and prefrontal alpha powers;

(iii) characterizing the subject's sustained focused attention by EEG measurement of the subject's frontal midline theta power;

(iv) characterizing the subject's neurocognitive, strategy by EEG measurement of left to right and anterior to posterior ratios of the subject's alpha powers;

(v) characterizing the subject's cognitive speed by EEG measurement of the subject's fronto-central P200 and P300 evoked potential peak latencies;

(vi) characterizing the subject's transient focused attention by EEG measurement of the subject's fronto-central P200 and P300 evoked potential amplitudes;

(vii) characterizing how the subject's brain and behavior respond to changes in mental workload by presenting more and less difficult versions of the same task during the same test session and measuring differences between the difficulty levels, and the difficulty levels and resting, in neural activity measures i–vi; and (viii) characterizing the subject's quickness to adapt by measuring changes in the neural activity measures i–vii as the subject continues to perform the attention demanding tasks during the same test session.

References Cited

McEvoy, L. K., Smith, M. E., & Gevins, A. (2000). Test-retest reliability of task-related EEG. *Clinical Neurophysiology*, 1, 457–463.

Gevins, A., & Smith, M. E. (1999). Detecting transient cognitive impairment with EEG pattern recognition. *Aviation, Space, and Environmental Medicine*, 70, 1018–1024.

Smith, M. E., McEvoy, L., & Gevins, A. (1999). Neurophysiological indices of strategy development and skill acquisition. *Cognitive Brain Research*, 7, 389–404.

McEvoy, L. Smith, M. E. & Gevins, A. (1998) Dynamic cortical networks of verbal and spatial working memory. *Cerebral Cortex*, 8, 563–574.

Gevins, A., Smith, M. E., Leong, H., et al. (1998). Monitoring working memory load during computer based tasks with EEG pattern recognition methods. *Human Factors*, 40 (1),79–91.

Gevins, A., Smith, M. E., McEvoy, L., & Yu, D. (1997). High resolution EEG mapping of cortical activation related to working memory. *Cerebral Cortex*, 7, 374–385.

Gevins, A. S., Smith, M. E., Le, J., Leong, H., Bennett, J., Martin, N., McEvoy, L., Du., R., & Whitfield, S. (1996)

High resolution evoked potential imaging of the cortical dynamics of human working memory. *Electroencephalography and Clinical Neurophysiology,* 98 (4), 327–348.

What is claimed is:

1. The method of measuring a subject's working memory, substantially free of bias from cultural and educational experience, to determine the subject's overall cognitive ability ("general intelligence"), including the steps of:
   (a) presenting an attention-demanding task to the subject, which engages the subject's working memory processes, and, simultaneously;
   (b) measuring the subject's behavioral responses to the task and neuroelectric activity at the subject's scalp using a set of electroencephalograph (EEG) electrodes and amplifier and analog/digital(A/D) converters to provide a set of digital data representing the subject's behavioral responses and neuroelectric activity in response to the task;
   (c) in a computer system, comparing the subject's digital data representing behavioral responses and neuroelectric activity in response to the task to a set of digital data representing the behavioral responses and EEG derived neuroelectric activity responses of a normal group to the same task; and
   (d) displaying the subject's overall cognitive ability score or scores based upon the comparison of (c) with the normal group.

2. The method of claim 1, wherein in (a) a passive control condition is presented to the subject for comparison to the attention-demanding task.

3. The method of claim 1 employed to measure changes in the subject's overall cognitive ability over a period of time, including performing the steps (a)–(c) to obtain a baseline cognitive ability score or scores and subsequently again performing the steps (a)–(c) to obtain a second cognitive ability score or scores and comparing the second and baseline cognitive ability scores.

4. The method of claim 1 employed to measure changes in the subject's overall cognitive ability over a period of time, including performing the steps (a)–(c) to obtain a prior cognitive ability score or scores and subsequently again performing the steps (a)–(c) to obtain a subsequent cognitive ability score and comparing the prior and subsequent cognitive ability scores.

5. The method of claim 1 employed to measure changes in the subject's overall cognitive ability over a period of time, including performing the steps (a)–(c) a plurality of times to obtain a prior set of cognitive ability scores and subsequently again performing the steps (a)–(c) to obtain a subsequent cognitive ability score or scores and comparing the subsequent cognitive ability score or scores with the prior set of scores.

6. The method of claims 2, 3, 4 or 5 employed to test the effect of medicine on a subject in which at least one score is obtained before administration of the medicine to the subject and at least another score is obtained after administration of the medicine to the subject.

7. The method of claims 2, 3, 4 or 5 employed to test the effectiveness of a remedial program to improve cognitive functioning in which at least one score is obtained before administration of the remedial program to the subject and at least another score is obtained after administration of the remedial program.

8. The method of claims 2, 3, 4 or 5 employed to measure the effect of fatigue on a subject in which at least one score is obtained when the subject is in an alert, rested state and at least another score is obtained after the subject has been deprived of a normal amount of sleep or is otherwise fatigued.

9. The method of claims 2, 3, 4 or 5 employed to measure the effect of injury or disease on a subject in which at least one score is obtained when the subject is in a healthy, uninjured state and at least another score is obtained after the subject has been injured or contracted a disease.

10. The method of claims 2, 3, 4 or 5 employed to measure recovery from injury or disease in which at least one score is obtained after the subject has been injured or contracted a disease and at least another score is subsequently obtained.

11. The method of claims 2, 3, 4 or 5 wherein the task is not culturally biased as it does not involve reading a language.

12. The method of claims 2,3,4 or 5 and presenting the subject with at least two versions of the task, one version being relatively more difficult than the other version.

13. The method of claims 2, 3, 4 or 5 and additionally presenting the subject with control conditions in which the subject sits passively with eyes opened and the with eyes closed.

14. The method of claims 2,3,4 or 5 and measuring the subject's neuroelectric activity in (b) while performing the task of (a) to determine one, or more, of the group selected from:
   i. characterizing the subject's level of alertness;
   ii. characterizing the subject's mental efforts and brain utilization;
   iii. characterizing the subject's sustained focused attention;
   iv. characterizing the subject's neurocognitive strategy;
   v. characterizing the subject's cognitive speed;
   vi. characterizing the subject's transient focused attention;
   vii. characterizing how the subject's brain and behavior respond to changes in mental workload by presenting more and less difficult versions of a task during the same test session;
   viii. characterizing the subject's quickness to adapt by presenting repeated trials of the same task during one test session.

15. The method of claims 2, 3, 4 or 5 and measuring the subject's neuroelectric activity in (b) while performing the task of (a) to determine one, or more, of the group selected from:
   i. characterizing the subject's level of alertness by EEG measurement of the subject's frontal delta power associated with slow horizontal eye movements, posterior theta and delta power, and ratios of posterior theta to alpha and delta to alpha powers;
   ii. characterizing the subject's mental effort and brain utilization by EEG measurement of the subject's parietal and prefrontal alpha powers;
   iii. characterizing the subject's sustained focused attention by EEG measurement of the subject's frontal midline theta power;
   iv. characterizing the subject's neurocognitive strategy by EEG measurement of left to right and anterior to posterior ratios of the subject's alpha powers;
   v. characterizing the subject's cognitive speed by EEG measurement of the subject's fronto-central P200 and P300 evoked potential peak latencies;
   vi. characterizing the subject's transient focused attention by EEG measurement of the subject's fronto-central P200 and P300 evoked potential amplitudes;
   vii. characterizing how the subject's brain and behavior respond to changes in mental workload by presenting more and less difficult versions of the same task during the same test session and measuring differences between the difficulty levels, and the difficulty levels and resting, in neural activity measures i–vi; and viii. characterizing the subject's quickness to adapt by measuring changes in the neural activity measures i–vii as the subject continues to perform the attention demanding tasks during the same test sessions.

16. The method of measuring the working memory of a subject, substantially free of bias from cultural and educational experience, to identify existing deficits and to determine the changes in the subject's working memory due to an underlying deleterious and/or progressive clinical condition, or due to any consequences of the administration of a medicine or remedial program, including the steps of:

(a) presenting to the subject an attention-demanding task, which engages the subject's working memory processes;

(b) before administration of the medicine-or remedial program measuring the subject's behavioral responses to the task questions and neuroelectric activity at the subject's scalp using a set of electroencephalograph (EEG) electrodes and amplifiers and analog/digital (A/D) converters to provide a set of baseline digital data representing the subject's behavioral responses to the task questions and neuroelectric activity in response to the task;

(c) in a computer system, comparing the subject's behavioral and neuroelectric responses to the task questions to a normal group's behavioral and neuroelectric responses to the task questions to obtain the subject's baseline score;

(d) performing the steps (a)–(c) to obtain the subject's score based upon a second or subsequent set of digital data and comparing the second or subsequent scores with the baseline score to obtain a measure of change of the subject's working memory due to administration of the medicine or the remedial program or changes over time;

(e) displaying the subject's changes in working memory based upon the comparison of the scores of (d).

17. The method of claim 16, wherein in (a) a passive control condition is presented to the subject for comparison to the attention-demanding task.

18. The method of claim 16 employed to test the effect of a medicine on a subject in which the baseline score is obtained before administration of the medicine to the subject and the second or subsequent score is obtained during or after administration of the medicine to the subject.

19. The method of claim 16 employed to test the effectiveness of a remedial program to improve cognitive functioning in which the baseline score is obtained before administration of the remedial program to the subject and the second or subsequent score is obtained during or after administration of the remedial program.

20. The method of claims 16–19 wherein the task is not culturally biased as it does not involve reading a language.

21. The method of claims 16–19 and presenting the subject with two versions of the task, one version being relatively more difficult than the other version.

22. The method of claims 16–19 and additionally presenting the subject with a control condition in which the subject sits passively with eyes opened and eyes closed.

23. The method of claim 16 employed to measure changes in the subject's working memory over a period of time to test an underlying deleterious and/or progressive clinical condition, including performing the steps (a)–(c) to obtain a prior score and subsequently again performing the steps (a)–(c) to obtain a subsequent score and comparing the prior and subsequent scores.

24. The method of claim 16 employed to measure changes in the subject's working memory to test an underlying deleterious and/or progressive clinical condition over a period of time, including performing the steps (a)–(c) a plurality of times to obtain a set of scores and subsequently again performing the steps (a)–(c) to obtain a subsequent score and comparing the subsequent score with the set of scores.

25. The method of claims 16–19 and measuring the subject's neuroelectric activity in (b) while performing the task of (a) to determine one, or more, of the group selected from:

i. characterizing the subject's level of alertness;

ii. characterizing the subject's mental efforts and brain utilization;

iii. characterizing the subject's sustained focused attention;

iv. characterizing the subject's neurocognitive strategy;

v. characterizing the subject's cognitive speed;

vi. characterizing the subject's transient focused attention;

vii. characterizing how the subject's brain and behavior respond to changes in mental workload by presenting more and less difficult versions of a task during the same test session;

viii. characterizing the subject's quickness to adapt by presenting repeated trials of the same task during one test session.

26. The method of claims 16–19 and measuring the subject's neuroelectric activity in (b) while performing the task of (a) to determine one, or more, of the group selected from:

(i) characterizing the subject's level of alertness by EEG measurement of the subject's frontal delta power associated with slow horizontal eye movements, posterior theta and delta power, and ratios of posterior theta to alpha and delta to alpha powers;

(ii) characterizing the subject's mental effort and brain utilization by EEG measurement of the subject's parietal and prefrontal alpha powers;

(iii) characterizing the subject's sustained focused attention by EEG measurement of the subject's frontal midline theta power;

(iv) characterizing the subject's neurocognitive, strategy by EEG measurement of left to right and anterior to posterior ratios of the subject's alpha powers;

(v) characterizing the subject's cognitive speed by EEG measurement of the subject's fronto-central P200 and P300 evoked potential peak latencies;

(vi) characterizing the subject's transient focused attention by EEG measurement of the subject's fronto-central P200 and P300 evoked potential amplitudes;

(vii) characterizing how the subject's brain and behavior respond to changes in mental workload by presenting more and less difficult versions of the same task during the same test session and measuring differences between the difficulty levels, and the difficulty levels and resting, in neural activity measures i–vi; and (viii) characterizing the subject's quickness to adapt by measuring changes in the neural activity measures i–vii as the subject continues to perform the attention demanding tasks during the same test session.

* * * * *